US008014962B2

(12) United States Patent
Ito et al.

(10) Patent No.: US 8,014,962 B2
(45) Date of Patent: *Sep. 6, 2011

(54) METHOD AND APPARATUS FOR ANALYZING MULTI-CHANNEL CHROMATOGRAM

(75) Inventors: Masahito Ito, Hitachinaka (JP);
Kisaburo Deguchi, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 525 days.

This patent is subject to a terminal disclaimer.

(21) Appl. No.: 12/073,964

(22) Filed: Mar. 12, 2008

(65) Prior Publication Data
US 2008/0172186 A1    Jul. 17, 2008

Related U.S. Application Data

(63) Continuation of application No. 11/501,750, filed on Aug. 10, 2006, now Pat. No. 7,356,446, which is a continuation of application No. 11/182,855, filed on Jul. 18, 2005, now Pat. No. 7,110,886, which is a continuation of application No. 10/115,080, filed on Apr. 4, 2002, now Pat. No. 6,934,638, which is a continuation of application No. 08/811,486, filed on Mar. 5, 1997, now Pat. No. 6,393,368, which is a continuation of application No. 08/409,986, filed on Mar. 24, 1995, now Pat. No. 5,644,503.

(30) Foreign Application Priority Data

Mar. 28, 1994 (JP) ........................................ 6-057313
Apr. 28, 1994 (JP) ........................................ 6-091064

(51) Int. Cl.
*G06F 19/00* (2006.01)

(52) U.S. Cl. ............. 702/23; 702/30; 702/32; 73/61.52; 73/61.58; 73/23.35; 73/23.36

(58) Field of Classification Search .................... 702/23, 702/32, 30; 73/61.52, 61.58, 23.35, 23.36
See application file for complete search history.

(56) References Cited

U.S. PATENT DOCUMENTS 4,353,242 A    10/1982    Harris et al. ................... 73/23.1
(Continued)

FOREIGN PATENT DOCUMENTS

EP    560533 A2 *    9/1993

OTHER PUBLICATIONS

Kalombet et al.: *Computer Spectrochromatography principles and Practice of Multichannel Chromatographic Data Processing*, Journal of Chromatography, V. 542, No. 2, pp. 247-261 Apr. 1991.

(Continued)

*Primary Examiner* — Carol S Tsai
(74) *Attorney, Agent, or Firm* — Kenyon & Kenyon LLP

(57) ABSTRACT

A method for analyzing a multi-channel chromatogram is realized for accurately resolving overlapping peaks on a multi-channel chromatogram to permit analysis of the composition of a sample. First, components of overlapping peaks are specified. A data matrix Dij is determined, and compressed in the wavelength direction to obtain a data matrix vector Di. Next, the two-dimensional data is deconvoluted, final standard deviation s0 is registered, and the deconvoluted two-dimensional data is reconvoluted to a retention intensity matrix. A quantitative spectral intensity matrix is computed, components are identified, and the identified components are quantified. Subsequently, an eigenvalue problem is solved, and the number n of components is estimated. The deconvolution and computation of the eigenvalue problem are iteratively executed until the peaks are isolated. Then, elution profiles are calculated, the components are identified, and the identified components are quantified.

20 Claims, 19 Drawing Sheets

U.S. PATENT DOCUMENTS

| | | | | |
|---|---|---|---|---|
| 4,363,242 A | * | 12/1982 | Heyman | 73/761 |
| 4,466,742 A | * | 8/1984 | Lemelson | 368/10 |
| 4,468,742 A | | 8/1984 | Jenden et al. | 702/23 |
| 4,617,032 A | * | 10/1986 | Wells | 95/89 |
| 4,631,687 A | * | 12/1986 | Kowalski et al. | 702/28 |
| 4,740,903 A | * | 4/1988 | Nakatsuka et al. | 702/32 |
| 4,752,888 A | * | 6/1988 | Yoshihara | 702/32 |
| 4,802,102 A | * | 1/1989 | Lacey | 702/32 |
| 4,807,148 A | * | 2/1989 | Lacey | 702/32 |
| 4,837,726 A | * | 6/1989 | Hunkapiller | 702/32 |
| 4,941,101 A | * | 7/1990 | Crilly | 702/32 |
| 5,076,909 A | * | 12/1991 | Overfield et al. | 208/177 |
| 5,119,316 A | | 6/1992 | Dam et al. | 364/498 |
| 5,175,430 A | | 12/1992 | Enke et al. | 250/282 |
| 5,293,580 A | * | 3/1994 | Shimizu | 382/243 |
| 5,311,445 A | * | 5/1994 | White | 702/28 |
| 5,400,265 A | | 3/1995 | Kauppinen | 364/498 |
| 5,498,875 A | | 3/1996 | Obremskie et al. | 250/458.1 |

OTHER PUBLICATIONS

Barker et al.: *Resolution of a Coeluting Chromatographic Pair Using Kalman Filtering*, Journal of Chromatography, v. 469, pp. 77-90, 1989.

Feng et al.: *Direct Deconvolution of Tung's Integral Equation Using a Multi-Gaussian Function Model for Instrumental Band Broadening in Gel-Permeation Chromatography*, Journal of Chromatography, v. 522, pp. 57-65, 1990.

Tyczkowska et al.: *Analysis of Cephalexin from Canine Skin Giopsy by Liquid Chromatography with Ultraviolet-Visible Photodiode-Array Detection*, J. Chromatogr. 427 (1), pp. 103-112, 1988

Janzen: *Recovering Corrupted Waveforms6*, C. Users Journal, v. 11, n. 6, p. 39(8), Jun. 1993.

Crilly: *A Comparative Study of Relaxation Based Iterative Deconvolution Methods*, System Theory, 1990, Twenty-Second Southeaster Symposium, pp. 545-549, Mar. 11-13, 1990.

* cited by examiner

RETENTION INTENSITY MATRIX R'ik FOR K-COMPONENT

COMPONENT1

RECONVOLUTION USING $h_i(\sigma_0)$
$R'_{ik} = h_i(\sigma_0) * r_{ik}(\sigma_0)$

COMPONENT2

COMPONENT3

SPECTRAL INTENSITY
MATRIX $X_{ij}$ FOR K-COMPONENT $$X' = (R'^T R')^{-1} R'^T D$$

CHARACTERISTIC VECTOR
WHEN $\sigma=0$
(ABSTRACT ELUTION
PROFILE MATRIX V)

FIRST PRINCIPAL COMPONENT

CHARACTERISTIC VECTOR
WHEN $\sigma=0$
(ABSTRACT ELUTION
PROFILE MATRIX V)

SECOND PRINCIPAL COMPONENT

DECONVOLUTED
CHARACTERISTIC
VECTOR

FIRST PRINCIPAL COMPONENT

DECONVOLUTED
CHARACTERISTIC
VECTOR

SECOND PRINCIPAL COMPONENT

ELUTION PROFILE MATRIX Y

COMPONENT 1

ELUTION PROFILE MATRIX Y

COMPONENT 2

PROCESSED ELUTION
PROFILE MATRIX y

COMPONENT 1

PROCESSED ELUTION
PROFILE MATRIX y

COMPONENT 2

CHANGES IN MATCHING DEGREE
RELATIVE TO STANDARD DEVIATION $\sigma$ $\zeta - \sigma$ PLOT

SCHEMATIC DIAGRAM FOR DETERMINING APPROPRIATENESS OF DECONVOLUTION PROCESSING

MATRIXES TO BE INVARIATE V.R

SCHEMATIC DIAGRAM FOR DETERMINING APPROPRIATENESS OF ENTIRE DFA (EQUATIUON A)
STRUCTURE OF
TRANSFORMATION T

T=N,R
N:NORMALIZED MATRIX
  (DIAGONAL MATRIX FOR
   NORMALIZING Y TO AREA 1)
R:ROTATION MATRIX (ORTHOGONAL
   OR OBLIQUE ROTATION)

FOOT

METHOD AND APPARATUS FOR ANALYZING MULTI-CHANNEL CHROMATOGRAM

This is a continuation of application Ser. No. 11/501,750 filed 10 Aug. 2006 now U.S. Pat. No. 7,356,446, which is a continuation of application Ser. No. 11/182,855 filed 18 Jul. 2005, U.S. Pat. No. 7,110,886, which is a continuation of application Ser. No. 10/115,080 filed 4 Apr. 2002, U.S. Pat. No. 6,934,638 B2, which is a continuation of application Ser. No. 08/811,486 filed 5 Mar. 1997, U.S. Pat. No. 6,393,368, which is a continuation of application Ser. No. 08/409,986 filed 24 Mar. 1995, U.S. Pat. No. 5,644,503.

BACKGROUND OF THE INVENTION

The present invention relates generally to chromatographic techniques such as high speed liquid chromatography and gas chromatography, and more particularly to methods and apparatuses for analyzing a multichannel chromatogram which is detected by a diode array detector or the like.

A large number of approaches have been proposed for separating or resolving overlapping peaks on a multi-channel chromatogram. The multichannel chromatogram refers to a type of a chromatogram having three-dimensional information composed of an absorbance component, a time component, and a wavelength component. Representatives of such approaches include factor analysis and principal component analysis which are techniques of multivariate analysis (see, for example, U.S. Pat. No. 4,807,148 issued to J. K. Strasters et al.; H. R. Keller et al, Journal of Liquid Chromatography, No. 12, pp. 3-22 (1988); J. Craig Hamilton et al., Chemometrics and Intelligent Laboratory Systems, No. 12, pp. 209-224 (1992); Journal of Chemometrics, No. 4, pp. 1-13 (1990), and so on).

A non-linear least-squares analysis has also been proposed as another approach for analyzing a multichannel chromatogram (see, for example, Itoh et al, Abstracts of Seventh Liquid Chromatography Conference, pp. 5 (1986); Itoh et al, Abstracts of 22th Applied Spectrometry Tokyo Conference, pp. 141 (1987); and Itoh et al, Abstracts of 19th HPLC Research Conversation, pp. 30 (1988)). This approach has been developed from a method for fitting overlapping peaks on a multichannel chromatogram obtained from GS/MS using the Gaussian (normal distribution function), which was proposed by F. J. Knorr, by substituting EMG (Exponentially Modified Gaussian) as a more realistic model function for the former Gaussian. This approach will be explained here in detail since it will facilitate the understanding of later descriptions.

Multichannel chromatogram data gathered from a diode array detector is given by the following matrix Dij (1):

$$D=R\cdot A\cdot S=R\cdot X \quad (1)$$

where i represents a time index, j a wavelength index, k a component index, Dij the absorbance, Rik a normalized retention waveform (chromatogram magnitude), Akk a quantitative factor relative to the concentration of a k-component, Skj a normalized spectral intensity, and Xkj a quantitative spectral intensity multiplied with the factor Akk relative to the concentration of a k-component. It should be noted that the wavelength index j is used as an index of the m/z value when a mass spectrometer is used.

Here, a trial matrix R'ik is introduced in place of the chromatogram intensity matrix Rik. From the equation (1), a trial spectral intensity matrix X'jk can be computed from the trial matrix R'kl and the matrix Dij containing the measured data. Consequently, a trial data matrix D'ij can be obtained as expressed by the following equation (2):

$$D'=R'\cdot(R'^T\cdot R')^{-1}\cdot R'^T D \quad (2)$$

where T in $R'^T$ means a transpose matrix, and −1 in $(R'^T\cdot R')^{-1}$ means that the associated matrix is an inverse matrix.

The least-squares method determines parameters so as to minimize Dij-D'ij and provides the best-fit R'ik for each component. In this way, the respective component matrices R'ik and X'ik can be separated or resolved from the matrix Dij including data on overlapping peaks.

This approach utilizes EMG which can also represent a asymmetric tailing peak as the R'ik matrix (the following equation (3)).

$$R'_{ik}=1/(\tau_k\sigma_k(2\pi)^{1/2})\int_0^{t_1}\exp[-(t_i-t_{RK}-t')^2]/2\sigma_k^2-t'/\tau_k)]dt' \quad (3)$$

where $t_{RK}$ is retention time for a k-component, $\sigma_K$ standard deviation for the k-component, and $\tau_K$ the time constant for the k-component.

JP-A-60-2447 describes a chromatographic quantitative analyzing method and apparatus which detect temporal changes in absorbance at multiple wavelengths as three-dimensional information to perform quantitative analysis. The chromatographic quantitative analyzing method and apparatus employ functions $f1(\lambda)$ and $f2(\lambda)$ which represent two previously measured two-dimensional standard spectra. Then, an equation is obtained for a two-dimensional synthesized component function $fs(\lambda)$ of a measured sample having overlapping peaks using the above-mentioned functions $f1(\lambda)$ and $f2(\lambda)$. The overlapping peaks are resolved by the obtained equation.

Other approaches utilizing deconvolution have also been proposed as a method for analyzing an ordinary chromatograin, i.e., a chromatogram having two-dimensional information (composed of an absorbance component and a time component). See, for example, U.S. Pat. No. 4,941,101 issued to Paul Benjamine Crilly; Paul Benjamine Crilly, IEEE Transaction on Instrumentation and Measurement, No. 40, pp. 558-562 (1991); and Journal of Chemometrics, No. 5, pp. 85-95 (1991).

Here, the convolution is defined. Original data is detected by a detector, and dispersed by an inherent device function h(t) (dispersion function(instrument function)) which represents the detection characteristics of the detector. The deconvolution is determined to be the processing for removing a dispersion portion of the data by the device function h(t) from the dispersion data. An equation defining the deconvolution is given in the following equation (4):

$$D(t)=\int_{-\infty}^{\infty}h(t')d(t-t')dt' = h(t)*d(t) \quad (4)$$

where D(t) is a detected waveform, d(t) an original waveform, and h(t) a dispersion function.

For the convolution applied to analysis on a chromatogram having two-dimensional information, several approaches have been proposed for promoting the convergence. Specifically, these approaches have been proposed principally relying on iteration methods, and include the Gaussian elimination which performs an inverse matrix operation, as well as Jacobi's method, Gauss-Seidel's method, Fourier Transform method, Van Cittert's method, Constrained Iterative method, Jansson's method, Gold's ratio method, and so on. For details of these methods, see "Waveform Data Processing for Scientific Measurements", edited by Shigeo Minami, published by CQ Editorial, pp. 122-139 (1986); and P. A. Jansson, "Deconvolution with Applications in Spectroscopy, New York, Academic (1984).

Also, a method based on factor analysis for separating or resolving overlapping peaks on a multichannel chromatogram is introduced in detail, for example, by Edmund R. Malinowski, "Factor Analysis in Chemistry", John Wiley & Sons, Inc. (1991).

This factor analysis based method is multivariate analysis, and its basic thinking is that a data matrix D is modeled as a product of a spectral matrix X and an elution profile matrix Y, as represented by the following equations (5) and (6). It should be noted however that the equation (6) defines that each component k is normalized to a peak area of one. However, since the data matrix D cannot be uniformly resolved from a mathematical point of view, several rational constraints are provided to solve the problem.

$$D = XY \tag{5}$$

$$\sum_j Y_{kj} = Y_k = 1 \tag{6}$$

where Dij: Signal Magnitude;
Xik: Spectral Intensity;
Ykj: Elution Profile;
i: Channel Index;
k: Component Index;
j: Time Index.

Generally, an eigenvalue problem is solved for the data matrix D, the number n of components is determined by principal component analysis, an abstract elution profile matrix V having a characteristic vector as its element is transformed by a matrix T, and thus a physically meaningful elution profile matrix Y is obtained. As the matrix Y is determined, the spectral matrix X can be computed from the data matrix D by the following equations (7)-(15).

More specifically, solving the eigenvalue problem, the data matrix D is represented by a product of an abstract spectral matrix U and the abstract elution profile matrix V as given by the following equation (7):

$$D = UV \tag{7}$$

Here, a characteristic vector of a product $Z=D^TD$, i.e., a product of a transposed matrix $D^T$ of the matrix D with the matrix D is $\vec{Vk}$. This vector $\vec{Vk}$ is a k'th row vector of the matrix V given by the following equation (8):

$$V = \begin{pmatrix} \vec{V1} \\ \vdots \\ \vec{Vk} \\ \vdots \\ \vec{Vn} \end{pmatrix} \tag{8}$$

Also, the relationship between a characteristic value ζk, the characteristic vector $\vec{Vk}$, and the matrix Z is given by the following equation (9):

$$Z\vec{Vk} = \zeta k \vec{Vk} \tag{9}$$

Further, the vector $\vec{Vk}$ is such that its sum of squares is normalized to one as given by the following equation (10):

$$\sum_j (V_{kj})^2 = |\vec{V_k}|^2 = 1 \tag{10}$$

The matrix V can be transformed to the matrix Y by a transformation matrix T as shown in the following equation (11):

$$Y = TV \tag{11}$$

where the matrix T is an n×n matrix.

The matrix T serves to perform an oblique rotation and a transformation for transforming the area of each raw vector in the matrix Y to one.

The matrix Y is represented by the following equation (12), where any component $\vec{Yk}$ of the matrix Y satisfies the following equation (13):

$$Y = \begin{pmatrix} \vec{Y1} \\ \vdots \\ \vec{Yk} \\ \vdots \\ \vec{Yn} \end{pmatrix} \tag{12}$$

$$\sum_j^n Y_{kj} = Y_k = 1 \tag{13}$$

Also, the matrix X is obtained from the matrices D and Y as shown in the following equation (14):

$$X = DY^T(YY^T)^{-1} \tag{14}$$

The matrices X, Y, U, and V have the relationship represented by the following equation (15)

$$D = XY = (UT^{-1})(TV) \tag{15}$$

The transformation matrix T, however, cannot be easily determined. Therefore, approaches as follows have been proposed for determining the transformation matrix T.

1. Methods with Known Spectrum:
1-1. TTFA (Target Transformation Factor Analysis): A method for determining a transformation matrix T such that a known spectral waveform is obtained from an abstract spectral matrix.
1-2. RAFA (Rank Annihilation Factor Analysis): A method for obtaining a known data matrix from standard forms of respective components and subtracting the components one by one from the obtained data matrix.
1-3. GRATA (Generalized Rank Annihilation Factor Analysis):
While RAFA (1-2) requires a data matrix having columns with one component, this approach enables curve resolution to be performed using a data matrix obtained from a standard mixed sample.
2. Modeling Methods with Unknown Spectrum:
2-1. Gaussian Non-linear Least-Squares Method: A method for performing a modeling on assumption that an elution profile is Gaussian, and the model is fit by the non-linear least-squares method.
2-2. Non-linear Least-Squares Method Using the Aforementioned EMG (Exponentially Modified Gaussian): A method identical to the above method 2-1 except for employing EMG which can represent asymmetric peaks in place of Gaussian.

3. Self Modeling Method with Unknown Spectrum:
3-1. ITTFA (Iterative Target Transformation Factor Analysis): A method which initially introduces a test vector having a pulsatile elution profile and gradually adjusts it to approach to a true elution profile.
3-2. EFA (Evolving Factor Analysis): A method which plots changes in the characteristic value along the time axis to find a stable region of the characteristic value. This stable region is called a window. An approach which fixes the outside of the stable region to zero to determine an elution profile for each component is particularly called WFA (Window Factor Analysis). For details of WFA, see E. R. Malinowski, J, Chemometrics, No. 6, pp. 29-40 (1992); and H. R. Keller et al., Anal. Chim, Acta., No. 246, pp. 379-390 (1991).
3-3. RAEFA (Rank Annihilation by Evolving Factor Analysis): A method which iterates the peak resolution performed by EFA (3-2) while subtracting components one by one from a data matrix.
3-4. RAFA Using Information Entropy as Index: A method which ranks down a matrix for each component, on the basis of minimum information entropy when obtaining an elution profile (see I. Sakura et al., J. Chromatogr, No. 506, pp. 223-243 (1990)).

SUMMARY OF THE INVENTION

However, although peak separation or resolution methods relying on the above-mentioned conventional least squares method are resistant to noise and suitable for practical use, a model function of any form must be introduced for the peak separation or resolution, so that it cannot be said that these methods always reproduce correctly actual peak shapes. Stated another way, while a model function is indispensable for the non-linear least-squares method, it is doubtful whether an employed model function is appropriate or not. Thus, the model function does not always give best-fit to actual peak shapes.

The problem of appropriateness also exists in the chromatographic quantitative analyzing method and apparatus described in JP-A-60-24447, and it cannot be said that the synthesized component function fs(l), employed therein, always correctly reproduces actual peak shapes, as is the case of the above-mentioned peak separation or resolution methods.

On the other hand, the deconvolution represented by Jansson's method is not resistant to noise. Introduced noise would be largely amplified during the deconvolution to cause pseudo-peaks to appear in a resultant graph. Thus, even if the conventional deconvolution is applied to the analysis on a three-dimensional multichannel chromatogram, noise components cannot be removed, so that accurate peak separation or resolution is hindered.

The above-mentioned factor analysis based method for separating or resolving overlapping peaks on a multi-channel chromatogram, in turn, has the following problems.
1. For employing the method with known spectrum, a standard spectrum need be known. This method cannot be applied if the spectrum is not known.
2. Since the modeling method with unknown spectrum requires a model function to be introduced for analysis, actual elution profiles are not always reproduced correctly.
3. The self modeling methods with unknown spectrum respectively imply various problems. Specifically, ITTFA in 3-1 and RAFA using information entropy as an index in 3-4 require a high resolution for overlapping peaks in a measured data matrix (see J. K. Strasters et al, Journal of Liquid Chromatography, No. 12 (1 & 2), pp. 3-22 (1989), I. Sakura et al). With a low resolution, these methods cannot ensure a meaningful solution because the calculation does not converge.
EFA in 3-2 and RAEFA in 3-3, on the other hand, are methods which assume that a region in which an elution profile presents zero is placed external to a window. Strictly speaking, however, the elution profiles do not include a zeroregion, although they may present values close to zero, so that the resolved result will include errors due to the assumption. In addition, it is difficult to clearly define a boundary between a zero-region and a non-zero region in practice.

It is therefore an object of the present invention to provide methods and apparatuses for analyzing a multi-channel chromatogram for highly accurately resolving overlapping peaks on a multichannel chromatogram to provide information useful in analyzing the components of a sample.

To achieve the above object, according to a first aspect, the present invention provides a method for analyzing a multi-channel chromatogram for analyzing chromatogram data having three-dimensional components composed of a characteristic component, a wavelength component, and a time component of a sample under measurement detected by a detector, which comprises the steps of compressing the chromatogram data having the three-dimensional components in terms of the wavelength component to transform to two-dimensional chromatogram data; performing deconvolution for removing a dispersion data portion due to an inherent device function representing the detection characteristic of the detector from the compressed two-dimensional chromatogram data; and identifying the characteristic component of the sample under measurement from the two-dimensional chromatogram data from which the dispersion data portion has been removed.

According to a second aspect, a method for analyzing a multichannel chromatogram of the present invention comprises the steps of compressing chromatogram data having three-dimensional components in terms of a wavelength component to transform the three-dimensional chromatogram data to two-dimensional chromatogram data; deconvoluting the compressed two-dimensional chromatogram to remove therefrom a dispersion data portion due to a normal distribution function which is an inherent device function of the detector representing its detection characteristic, and changing standard deviation of the normal distribution function to isolate overlapping peaks in the two-dimensional chromatogram data; performing convolution using the device function for adding dispersion data portions to respective components of the two-dimensional chromatogram data from which the dispersion data portion has been removed, to restore the data before the deconvolution; computing spectral information on the respective components based on the restored data; identifying the characteristic component of the sample under measurement from the computed spectral information and quantifying the characteristic component; and displaying at least the identified and quantified characteristic component and the restored data obtained by the convolution on display means.

According to a third aspect, a method for analyzing a multichannel chromatogram comprises the steps of performing deconvolution for removing a dispersion data portion due to an inherent device function representing the detection characteristic of a detector from three-dimensional chromatogram data; compressing the deconvoluted chromatogram data in terms of the time component to compute spectral information on the respective components; and identifying the characteristic component of the sample under measurement based on the computed spectral information.

According to a fourth aspect, an apparatus for analyzing a multichannel chromatogram for analyzing chromatogram data having three-dimensional components composed of a characteristic component, a wavelength component, and a time component of a sample under measurement detected by detector means, comprises a data compression unit for compressing the chromatogram data having the three-dimensional components in terms of the wavelength component to transform the three-dimensional chromatogram data to two-dimensional chromatogram data; a deconvolution unit for performing deconvolution for removing a dispersion data portion due to an inherent device function representing the detection characteristic of the detector means from the compressed two-dimensional chromatogram data; and a component identification unit for identifying the characteristic component of the sample under measurement from the two-dimensional chromatogram data from which the dispersion data portion has been removed.

Preferably, in the methods and apparatus for analyzing a multichannel chromatogram, the deconvolution unit or the deconvolution step changes standard deviation of a normal distribution function to isolate overlapping peaks in the two-dimensional chromatogram data.

Also, preferably, the methods and apparatus for analyzing a multichannel chromatogram further comprise a reconvolution unit and step for performing convolution using the device function for adding dispersion data portions to respective components of the two-dimensional chromatogram data from which the dispersion data portion has been removed, to restore the data before the deconvolution; and a display unit and step for displaying the identified characteristic component and the restored data obtained by the convolution, respectively.

According to another aspect, an apparatus for analyzing a multichannel chromatogram comprises a data setting unit for setting a start point and an end point for a time component of three-dimensional chromatogram data to be analyzed; a data compression unit for compressing chromatogram data having three-dimensional components set by the data setting unit in terms of the wavelength component to transform the three-dimensional chromatogram data to two-dimensional chromatogram data; a deconvolution unit for performing deconvolution for removing a dispersion data portion due to a normal distribution function which is an inherent device function representing the detection characteristic of a detector means, and changing standard deviation of the normal distribution function to isolate overlapping peaks in the two-dimensional chromatogram data; a separation/normalization unit for separating the deconvoluted chromatogram data into the respective components and normalizing the respective components; a reconvolution unit for executing convolution for adding a dispersion data portion to each of the components of the separated and normalized data to restore the data before the deconvolution; a spectrum computation unit for computing spectral information on the respective components based on the restored data; a component identification/quantification unit for identifying the characteristic component of the sample under measurement from the computed spectral information and quantifying the characteristic component; and display unit for displaying at least the identified and quantified characteristic component and the restored data obtained by the convolution.

Preferably, in the methods and apparatuses for analyzing a multichannel chromatogram, the display unit and step display the identified and quantified characteristic component, the compressed two-dimensional chromatogram data, the data on the respective components of the convoluted data, and the spectral information on the respective components.

Also preferably, in the methods and apparatuses for analyzing a multichannel chromatogram, the characteristic component of the sample under measurement is the absorbance.

According to a further aspect, an apparatus for analyzing a multichannel chromatogram comprises a data setting unit for setting a start point and an end point for each of a time component and a wavelength component of three-dimensional chromatogram data to be analyzed; a deconvolution unit for performing deconvolution for removing a dispersion data portion due to an inherent device function representing the detection characteristic of detector means from the three-dimensional chromatogram data to which the start points and the end points have been set; a normalized spectrum computation unit for normalizing the deconvoluted chromatogram data, compressing the normalized chromatogram data in terms of the time component, and computing spectral information on the respective components; and a component identification/quantification unit for identifying the characteristic component of the sample under measurement and quantifying the characteristic component.

Preferably, in the methods and apparatuses for analyzing a multichannel chromatogram, the device function is a normal distribution function.

Also preferably, the methods and apparatuses for analyzing a multichannel chromatogram further comprise display means and step for displaying the identified characteristic component and the spectral information on each component, respectively.

Also preferably, the methods and apparatuses for analyzing a multichannel chromatogram further comprise input means and step for inputting a region to be analyzed in the three-dimensional chromatogram data and a number of overlapping peaks to the data setting unit, respectively.

Also preferably, the methods and apparatuses for analyzing a multichannel chromatogram further comprise input means and step for inputting standard deviation of the device function, a plurality of retention times to be estimated, and an initial value of a fitting parameter for a time constant for specifying a tailing peak to the deconvolution unit.

According to a further aspect, a method for analyzing overlapping peaks on a multichannel chromatogram comprises the steps of deconvoluting the multichannel chromatogram using a predetermined dispersion function; performing multivariate analysis from the deconvoluted multichannel chromatogram; determining the width of the predetermined dispersion function and the deconvoluted multichannel chromatogram corresponding thereto in accordance with a criterion requiring that the peaks are isolated; and acquiring a spectral waveform from the determined multichannel chromatogram.

According to a further aspect, a method for analyzing overlapping peaks on a multichannel chromatogram comprises the steps of: deconvoluting the multichannel chromatogram using a predetermined dispersion function; factor-analyzing the deconvoluted multichannel chromatogram; determining whether a predetermined variate of the multichannel chromatogram is stable from the relationship between the width of the predetermined dispersion function and a resolution of the factor analysis corresponding thereto; determining the width of the dispersion function and the deconvoluted multichannel chromatogram in accordance with a criterion requiring that the peaks are isolated; and acquiring a spectral waveform from the determined multichannel chromatogram.

According to a further aspect, a method for analyzing overlapping peaks on a multichannel chromatogram comprises the steps of deconvoluting the multichannel chromatogram using a predetermined dispersion function; factor-analyzing the deconvoluted multichannel chromatogram; determining whether factor analysis corresponding to the width of the predetermined dispersion function uniquely has a solution; determining the width of the dispersion function and the deconvoluted multichannel chromatogram corresponding thereto in accordance with a criterion requiring that the factor analysis uniquely has a solution; and acquiring a spectral waveform from the determined multichannel chromatogram.

According to a further aspect, a method for analyzing overlapping peaks on a multichannel chromatogram comprises the steps of deconvoluting the multichannel chromatogram using a predetermined dispersion function; solving an eigenvalue problem from the deconvoluted multichannel chromatogram; determining whether the peaks are isolated from the relationship between the width of the dispersion function and a solution of the eigenvalue problem corresponding thereto; determining the width of the dispersion function and the deconvoluted multichannel chroinatogram corresponding thereto in accordance with a criterion requiring that the peaks are isolated; and acquiring elution profiles from the determined multichannel chromatogram.

According to a further aspect, a data processing apparatus for analyzing overlapping peaks on a multichannel chromatogram comprises a first memory for storing the width of a dispersion function; a convolution unit for convoluting the dispersion function stored in the first memory; a factor analysis unit for factor-analyzing the deconvoluted multi-channel chromatogram; a second memory for storing a solution of an eigenvalue problem of the factor-analyzed multichannel chromatogram; and an output unit for outputting a spectral waveform acquired from the deconvoluted multichannel chromatogram using the width of the dispersion function determined on the basis of the solution of the eigenvalue problem.

According to a further aspect, a data processing apparatus for analyzing overlapping peaks on a multichannel chromatogram comprises a first memory for storing the width of a dispersion function; a convolution unit for convoluting the dispersion function stored in the first memory; a factor analysis unit for factor-analyzing the deconvoluted multi-channel chromatogram; a second memory for storing a solution of an eigenvalue problem of the factor-analyzed multichannel chromatogram; and an output unit for outputting a spectral waveform acquired from the deconvoluted multichannel chromatogram using the width of the dispersion function determined on the basis of the solution of the eigenvalue problem.

In a multichannel chromatogram having three-dimensional components composed of a characteristic component of a sample under measurement, a wavelength component, and a time component, noise components included in the chromatogram negatively and positively fluctuate, i.e., increase and decrease in the wavelength component direction. If the multichannel chromatogram is compressed in the wavelength component direction, the noise components will cancel with each other. For this purpose, the multichannel chromatogram is compressed in terms of the wavelength component to be transformed into two-dimensional chromatogram data. This transformation removes the noise components. The two-dimensional chromatogram data having the noise components removed therefrom is subjected to the deconvolution for removing data dispersion due to the device function, thus accurately resolving overlapping peaks. Then, the components of the sample under measurement are identified based on the accurately resolved data.

The noise components included in the multichannel chromatogram having the three-dimensional components also negatively and positively fluctuate, i.e., increase and decrease in the time component direction. Therefore, the multichannel chromatogram is first subjected to the deconvolution. Then, the deconvoluted data is compressed in terms of the time component for each of the components, and spectral information is calculated for each component. The noise components cancel with each other in this process and they are thus removed from the data. Finally, the components of the sample under measurement are identified based on the spectra having the noise components removed therefrom.

A basic procedure of DFA will be next described.

1. A data matrix D is deconvoluted. The deconvolution is intended to deconvolute a dispersion function h from the data matrix D to obtain a deconvoluted data matrix d, as represented by the following equation (16):
   Deconvolution $$Dij=hi(\sigma)*dij(\sigma) \tag{16}$$

In the above equation, convolution of d with h results in the data matrix D. Replacing the discretely expressed time i by a continuous variable t and representing the deconvolution in an integration form, the following equation (17) is obtained. Note that convoluted matrices are represented in lower case letters:

$$D_i(t) = \int_{-\infty}^{\infty} h(t'; \sigma) d_i(t - t'; \sigma) dt' \tag{17}$$

Since the deconvolution is executed with the time t specified as a variable, the spectrum is processed for each channel with index i. Stated another way, each row vector of the matrix D is deconvoluted with the same dispersion function h.

It should be noted that in the case of chromatograms, Gaussian as expressed by the following equation (18) is normally used for the dispersion function h. Also, it is well known in the art to convolute a chromatogram using Gaussian as a dispersion function for resolving peaks.

$$h(t;\sigma)=(1/(\sqrt{2\pi}\sigma))e^{-(t^2/2\sigma^2)^2} \tag{18}$$

The mechanism of the dispersion is described in detail in "DYNAMICS OF CHROMATOGRAPHY" by J. C. Giddings, published by Marcel Dekker, New York, 1965.

2. Prior to the deconvolution, standard deviation s serving as a criterion for the extension of Gaussian must be determined. Simply, selected for this case may be such standard deviation that permits all overlapping peaks to be separated and isolated. Actually, if all peaks are isolated in either of channels, the characteristic vector expressed by the equation (7) corresponds to each component, so that the elution profile matrix y can be determined.

The spectral matrix X can also be obtained in accordance with the following equations:

$$d=Xy \tag{19}$$

$$X=dy^T(yy^T)^{-1} \tag{20}$$

where y is an elution profile matrix isolated by the deconvolution. The elution profile matrix y is obtained by rotating and normalizing the characteristic vector when isolated.

Since the elution profile matrix Y can be determined in accordance with the following equation (21), i.e., since the matrix Y can be obtained from the matrices D and X, the resolution of overlapping peaks is completed:

$$Y = (X^T X)^{-1} X^T D \qquad (21)$$

As an alternative approach, at the time the matrix y is determined, the dispersion function h used in the convolution is used to reconvolute isolated peaks to restore the original elution profile matrix Y (this processing is hereinafter called "reconvolution"). Subsequently, the spectral matrix X may be computed in accordance with the equation (14).

3. Ideally, all peaks on a chromatogram are isolated by executing once the deconvolution. However, actually, the isolation of peaks implies the following problems: (1) the number of components included in overlapping peaks is unknown; and (2) Generally, when the deconvolution is performed with a dispersion function h having unnecessarily large standard deviation σ, noise is extremely amplified. RAFA can be applied for solving these problems.

Alternatively, the matrix D is deconvoluted as the standard deviation s is gradually extended to obtain matrices d(σ). Each of the matrices d(σ) is subjected to factor analysis. As explained above, the transformation matrix T is generally indefinite. The transformation matrix has the nature of obtaining a physically meaningful elution profile matrix Y by orthogonal rotation transformation when peaks are isolated. Methods for finding out an appropriate orthogonally rotated transformation matrix T include "varimax", "quartimax", and so on. For example, the matrices d(σ) are sequentially factor-analyzed in the order of smaller σ. When a column vector in a obtained spectral matrix X presents a constant spectral waveform, determination can be made at this point that a peak is isolated. This constant column vector is determined as the spectrum of a first component, and the rank of the first component is degraded by one. Similar rank annihilation is repeated to complete the factor analysis for peak resolution.

Similarly, methods for determining oblique rotation (obliquemax, quartimin, biquartimin, covarimin, binormamin, maxplane, promax, and so on) may be used for factor analysis instead of orthogonal rotation. Alternatively, it is also possible to employ a criterion with which the characteristic vector becomes positive to the utmost, and the value of the following equation (22) becomes maximum:

$$\sum_k \sum_j \sqrt{|\xi_k|} \, v_{kj} \qquad (22)$$

Such a criterion has an advantage that the spectrum can be obtained even if peaks are not completely isolated, and small-scale deconvolution is sufficient to sequentially perform the rank annihilation.

In ordinary factor analysis, the spectral matrix X and the elution profile matrix Y cannot be uniquely obtained. The DFA employed by the present invention enables the matrices X and Y to be determined by performing deconvolution to isolate elution profiles corresponding to respective components. The essence underlying this approach is that the matrix D is the product of the matrices X and Y, and that when the matrix D is deconvoluted, the deconvolution actually acts only on the matrix Y. Since the matrix X is preserved when the elution profiles are isolated, a spectral waveform can be immediately generated. The matrix Y may be computed from the matrix D using the matrix X or may be obtained by reconvoluting isolated elution profiles. On the other hand, the deconvolution, when performed on a two-dimensional chromatogram, gives rise to a problem that pseudo-peaks are amplified. The DFA, however, extends its analysis to multichannel data so that noise components cancel with each other, thus eliminating the occurrence of pseudo-peaks. Further, the appropriateness of the processing itself can be evaluated by executing factor analysis simultaneously with the deconvolution. This evaluation is important since the present invention iteratively executes this processing. For example, when the matrix D is transformed to the matrix d, the matrix V is simultaneously transformed to the matrix v (abstract elution profiles after the processing). On the other hand, the matrix U remains invariant after the execution of this processing. As shown in the left half of FIG. 18, a matrix v obtained by solving the eigenvalue problem to obtain the matrix V from the data matrix D and deconvoluting the matrix V should be equal to a matrix V obtained by deconvoluting the data matrix D to obtain the matrix d and solving the eigenvalue problem for the matrix d. The appropriateness of the deconvolution can be evaluated by comparing these two matrices v. Alternatively, when a tolerable range is exceeded, the deconvolution may be corrected such that substantially tolerable results can be obtained from either of the paths, thus ensuring the matching of the two paths. The same can be applied to the right half of FIG. 18. By comparing two paths from the matrix V to the matrix y, the appropriateness of the deconvolution is evaluated and, if a tolerable range is exceeded, the deconvolution may be corrected to ensure the matching of the two paths. It should be noted however that since the transformation T is involved in this case, rotation over completely the same angle must be performed on the two paths. Generally, rotation R determined after the deconvolution is employed. By solving the eigenvalue problem with the approach described herein, the deconvolution can be corrected to be more appropriate such that pseudo peaks can be prevented to the utmost from occurring due to noise amplified by the deconvolution which has been a disadvantage of this processing.

Further, as shown in FIG. 19, the appropriateness of the entire DFA can be evaluated by examining whether a matrix y obtained by deconvoluting the matrix Y computed from the matrix D using the spectral matrix X (through the upper path) matches a matrix y obtained from the deconvoluted matrix d using the same matrix X (through the lower path).

DETAILED DESCRIPTION OF THE PREFERRED EMBODIMENTS

Embodiments based on the present invention will hereinafter be described with reference to the accompanying drawings.

Figure 1:
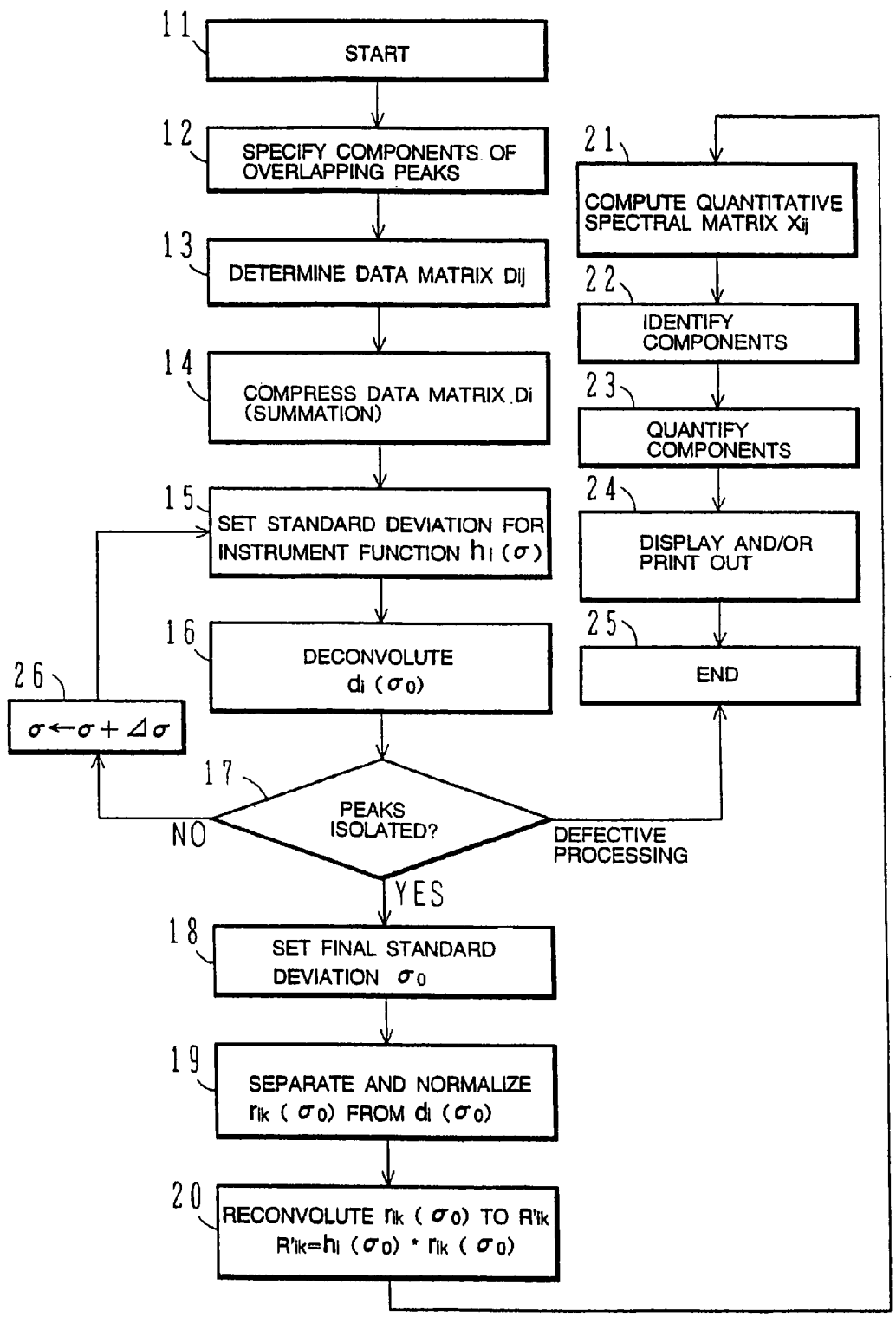
FIG. 1 is an operational flow chart representing a method for analyzing a multichannel chromatogram according to a first embodiment of the present invention.
Figure 2:
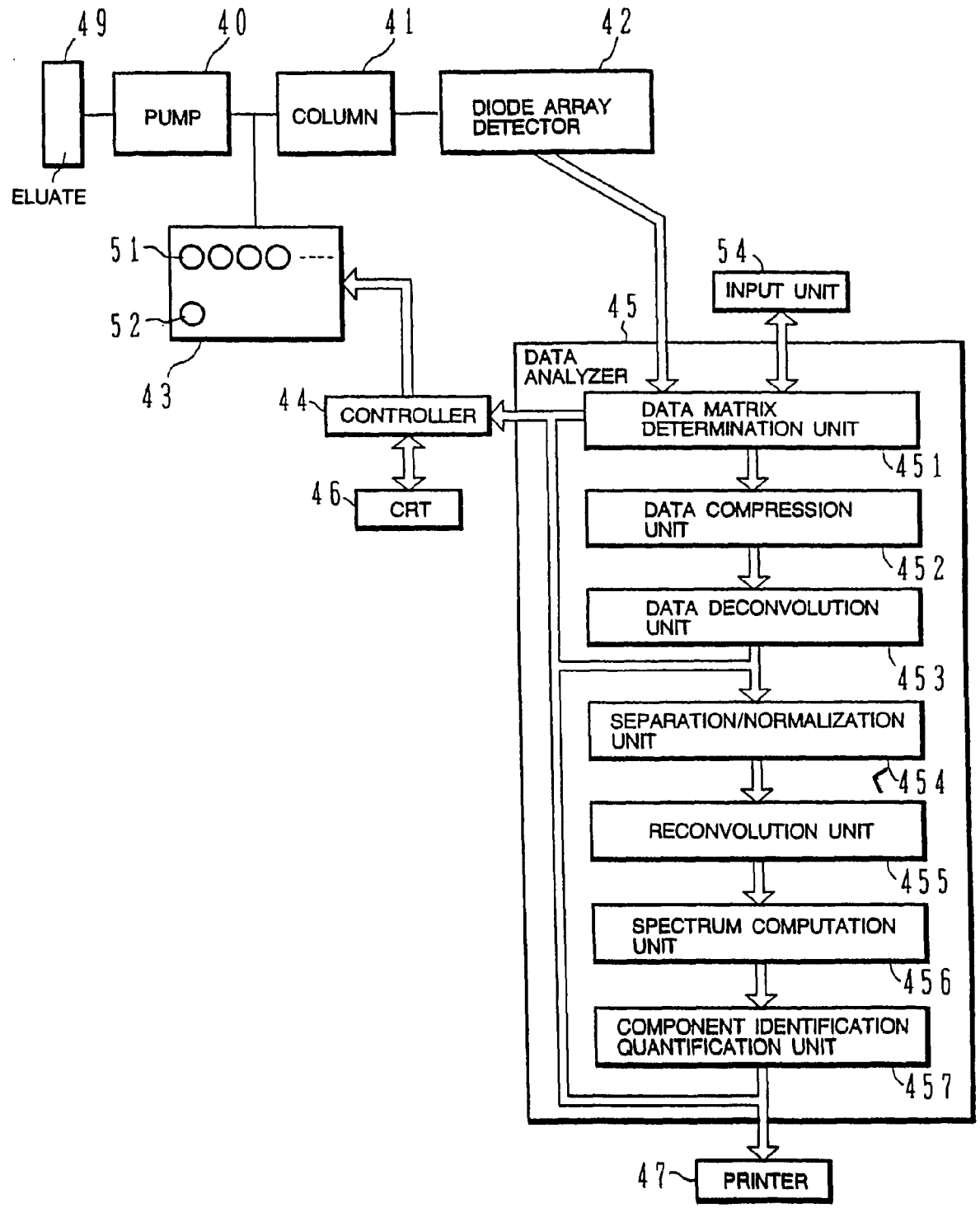
FIG. 2 is a block diagram schematically showing the configuration of an apparatus for analyzing a multichannel chromatogram according to the first embodiment of the present invention.

FIG. 1 is an operational flow chart representing a method for analyzing a multichannel chromatogram according to a first embodiment of the present invention, and FIG. 2 is a schematic diagram showing the configuration of an apparatus for analyzing a multichannel chromatogram according to the first embodiment of the present invention. More specifically, FIG. 2 shows an example wherein the present invention is applied to a medicament monitoring HPLC (High Performance Liquid Chromatography) system. It is assumed in this embodiment that the term "multichannel chromatogram" is defined to have three-dimensional components including an absorbance component (characteristic component), a wavelength component, and a time component.

Referring to FIG. 2, a pump 40, in response to a command from a controller 44, begins to deliver an eluate 49. A sampler 43 having a movable needle injects a standard sample 52 stored in a sample container or an unknown sample (sample under measurement) 51 to sweep it into a channel of a column 41. The sample 51 or 52 is swept into the column 41 together with the eluate 49, wherein its components are separated and extended, and then detected by a diode alley detector 42. A multichannel chromatogram, which is the data detected by the diode array detector 42, is supplied to a data analyzer 45. Also, the components and so on are supplied to the data analyzer 45 through an input unit 54, as will be later described.

The data analyzer 45 comprises a data matrix determination unit (data setting unit) 451, a data compression unit 452, a deconvolution unit 453, and a separation/normalization unit 454. The data analyzer 45 also includes a reconvolution unit 455, a spectrum computation unit 456, and a component identification/quantification unit 457. The results of analysis obtained by the data analyzer 45 are displayed on a CRT 46 or printed out by a printer 47.

Figure 3A:
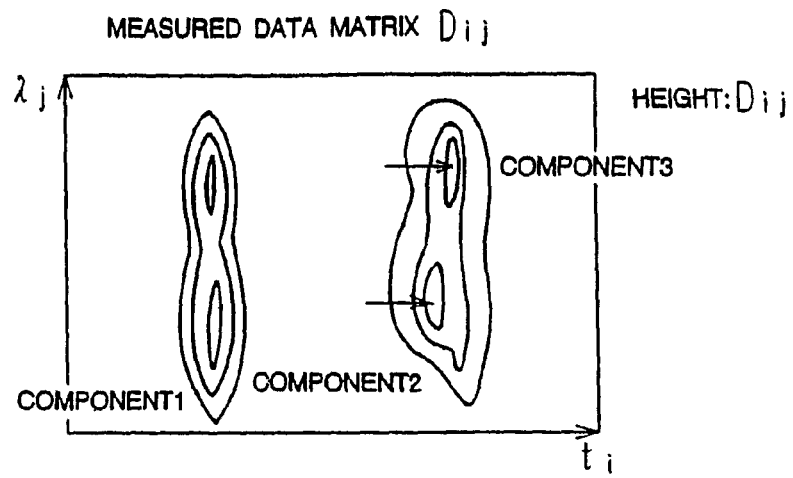
FIGS. 3A-3C are graphs showing examples of displayed multichannel chromatogram data.
Figure 3B:
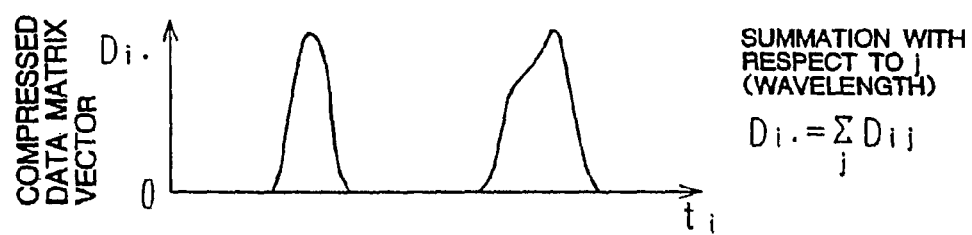
Figure 3C:
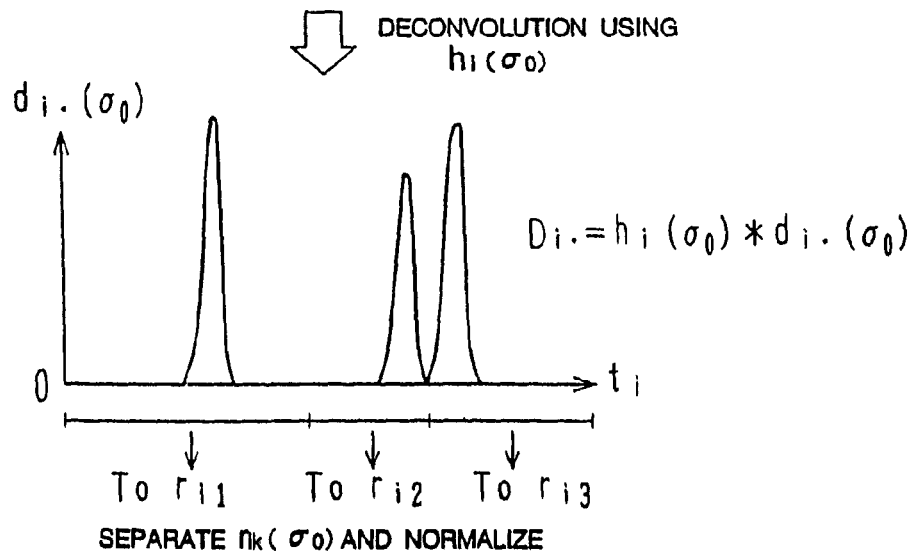
Figure 4A:
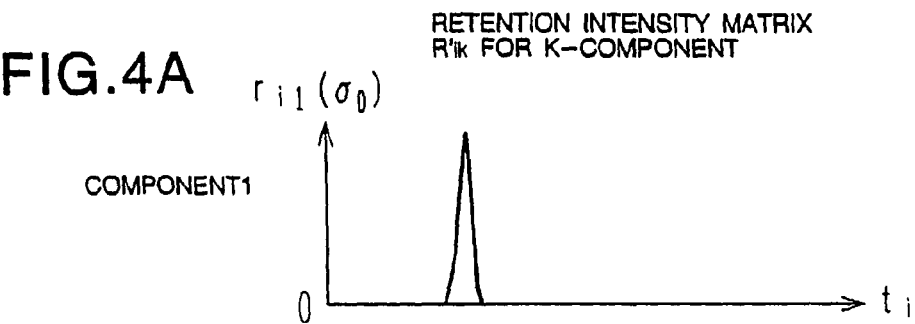
FIGS. 4A-4F are waveform charts each showing a retention intensity matrix for a reconvoluted component k.
Figure 4B:
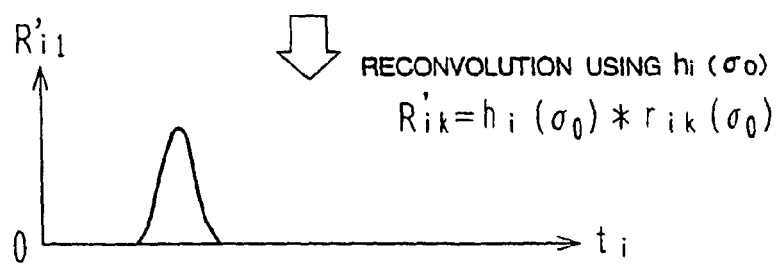
Figure 4C:
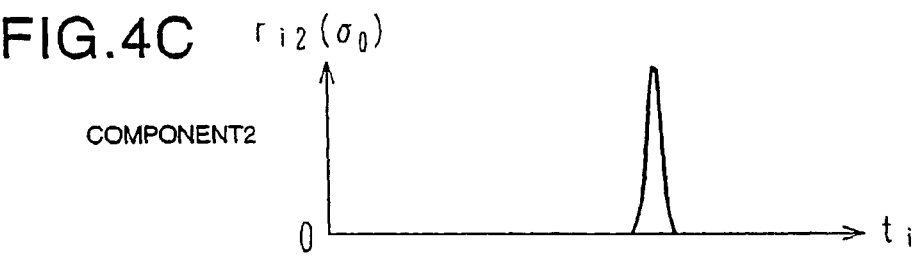
Figure 4D:
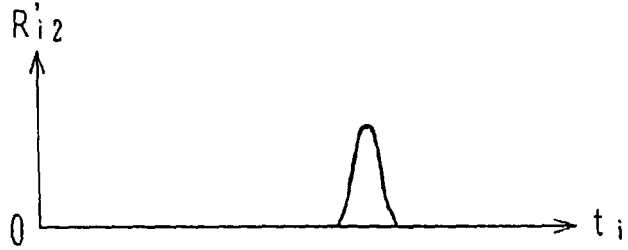
Figure 4E:
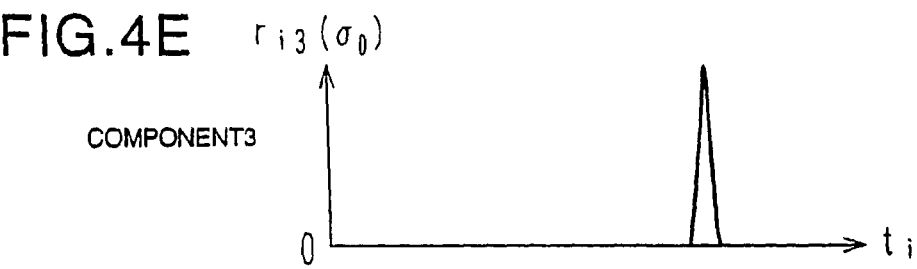
Figure 4F:
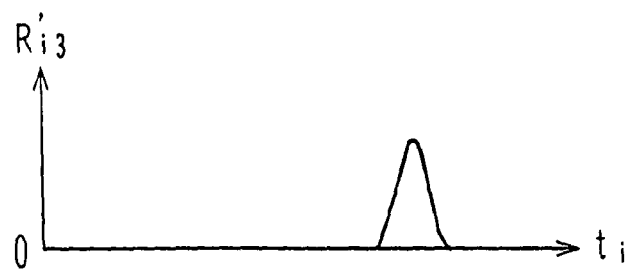

FIGS. 3-6 show a multichannel chromatogram of the unknown sample 51 resulted from the first embodiment of the present invention. Referring first to FIG. 3 (A), since components 2 and 3 overlap with each other, it is difficult to not only quantify but also identify them. For this reason, the overlapping peaks must be separated or resolved, a retention time be correctly obtained, and the spectra be accurately defined in order to identify the components. Also, by performing the separation or resolution of the components to accurately obtain the magnitudes of the peaks, a quantitative analysis may be carried out from a comparison with the standard sample 52.

Next, the procedure of an analyzing method and the operation of the apparatus, according to the first embodiment of the present invention, will be described with further reference to FIGS. 1-6.

In FIG. 2, multichannel chromatogram data is supplied from the diode array detector 42 to the controller 44 through the data matrix determination unit 451, and a contour plan of a three-dimensional chromatogram is displayed on the CRT 46 as shown in FIG. 3A. The operational flow of FIG. 1 is assumed to start with the state in which the contour plan is displayed on the CRT 46.

After the operational flow starts at step 11 of FIG. 1, overlapping peak components to be separated or resolved are specified at step 12. More specifically, the operator inputs overlapping peak components 2, 3 shown in FIG. 3 (A) through a keyboard, a mouse, a pen, or the like into the data matrix determination unit 451, with reference to the contour plan displayed on the CRT 46. Alternatively, the coordinates of peak components 2, 3 may be inputted in the form of numerical values or by moving a cursor over lines on which the peak components are displayed. By inputting peak components twice, the data matrix determination unit 451 determines that there are two overlapping peak components. Also, by this input operation, a valley is expected to be created between the two points at which the peaks are located, after deconvolution.

Subsequently, at step 13, the data matrix determination unit 451 searches for a start point and an end point of the whole area occupied by the specified overlapping components, determines a starting point and an end point in time of a data matrix Dij, shown in the aforementioned equation (1), to determine the data matrix Dij. An appropriate number of measuring points from the start point to the end point is in the range of 20-50. In case a larger number of points are required, the number of points is desirably reduced by an accumulative average or the like. As to a number of points in the wavelength direction, the number of measuring channels may be simply employed.

Next, at step 14, the data compression unit 452 compresses the data matrix Dij in the wavelength direction ($\lambda$ direction) in accordance with the following equation (23), i.e., sums up all components of the data matrix to obtain a compressed data column vector Di• (see FIG. 3 (B)):

$$D_i = \sum_{j=1}^{nj} D_{ij} \qquad (23)$$

Here, explanation will be given of the reason for which the data matrix Dij is compressed in the wavelength direction as expressed by the equation (23).

Although not shown, the multichannel chromatogram shown in FIG. 3 (A) generally include many noise components (noise components in the height direction). These noise components are thought to oscillate positively and negatively in the wavelength direction with respect to a predetermined reference level. Thus, the summation of the three-dimensional data in the wavelength direction will result in cancellation of such noise components to provide noise-free two-dimensional data Di•.

Next, the two-dimensional data Di• is subjected to deconvolution. This is because the two-dimensional data is thought to have been convoluted (dispersion) by the following equation (24-1), where σ is standard deviation, hi(σ) is a Gaussian-type device function expressed by the following equation (24-2), and di(σ) is an original two-dimensional data function.

$$D_{i\bullet} = h_i(\sigma)^* d_{i\bullet}(\sigma) \qquad (24\text{-}1)$$

$$h_i(\sigma) = (1/(\sqrt{2\pi}\sigma)) e^{-(n^2/2\sigma^2)} \qquad (24\text{-}2)$$

At step 15, the deconvolution unit 453 sets the standard deviation σ of the device function hi(σ). An initial value of the standard deviation σ may be set, for example, to a value equal to one tenth of a time difference between the two overlapping peak points specified at step 12. Alternatively, 1/30 of a time width of the Di• matrix, a fixed value, an input value, or the like may be selected for the initial value of the standard deviation s. Further alternatively, the initial value may be set to zero.

Subsequently, at step 16, the deconvolution unit 453 calculates a function di (σ) from the data Di and function hi(σ) in the equation (24-1). In other words, the data Di is deconvoluted. In this case, a method such as Jansson's method or the like may be unitized for the deconvolution.

Next, at step 17, the deconvolution unit 453 determines whether data row vectors after the deconvolution are sufficiently separated so that the overlapping peaks are isolated. As a criterion, determination is made as to whether a depth of a valley between the peaks is equal to or less than 3% of a maximum value. If this criteria is satisfied, the flow proceeds to step 18. Otherwise, the flow proceeds to step 26 to increase the standard deviation σ, returns to step 15, where the deconvolution is again attempted. An increment of the standard deviation σ may be, for example, the initial value of the standard deviation. It should be noted, however, that if the initial value of the standard deviation has been set to zero, an appropriate value other than zero should be selected for the increment.

If an abnormally gigantic pseudo peak or the like occurs at step 17, defective processing is determined. In this event, the deconvolution unit 453 transfers an error signal to the controller 44 to display the occurrence of an error on the CRT 46, followed by the flow proceeding to step 25, where the flow is terminated.

If the deconvolution unit 453 determines at step 17 that the peaks are isolated (a deconvoluted waveform is shown in FIG. 3 (c)), the flow proceeds to step 18, where the finally determined standard deviation is registered as a final standard deviation σ0.

Next, at step 19, the separation/normalization unit 454 uses the following equation (25-1) to calculate a normalized matrix rik(σ0) for each component from the isolated data di•(σ0). The separation or resolution in the method according to this embodiment are executed at this step, and the processing is traced back from the step 19 which is regarded as a turning point. Next, at step 20, the reconvolution unit 455 uses the same device function hi(σ0) as that used for the deconvolution to reconvolute each normalized matrix rik(σ0) to a retention intensity matrix R'ik in accordance with the following equation (25-2) (FIGS. 4A-4F). With this processing, the overlapping peak components detected by the detector can be represented as respective noise free waveforms.

$$d_{i\bullet}(\sigma_0) = \Sigma_k f_k r_{ik}(\sigma_0) \qquad (25\text{-}1)$$

$$R'_{ik} = h_i(\sigma_0)^* r_{ik}(\sigma_0) \qquad (25\text{-}2)$$

where fk is a factor.

Figure 5A:
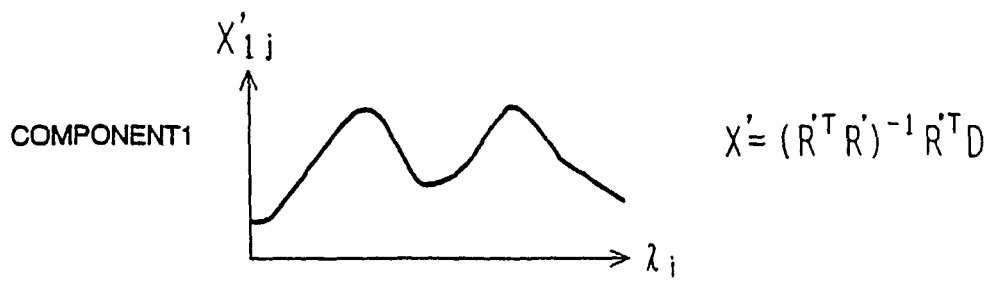
FIGS. 5A-5C are waveform charts each showing a spectral intensity matrix for a component k.
Figure 5B:
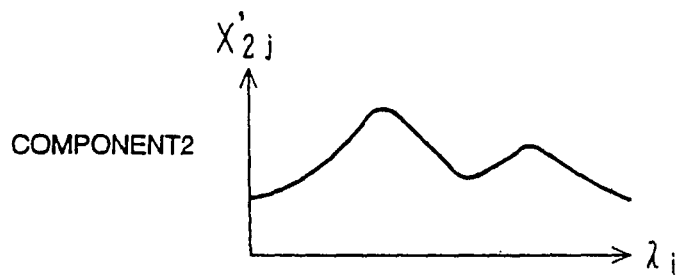
Figure 5C:
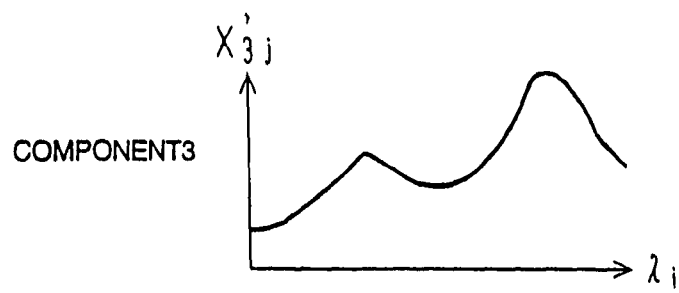

Subsequently, at step 21, the spectrum computation unit 456 computes a quantitative spectral intensity matrix X'kj for each component based on the following equation (26), as shown in FIGS. 5A-5C:

$$X' = (R'^T R')^{-1} R'^T D \qquad (26)$$

Next, at step 22, the component identification/quantification unit 457 identifies the components based on the spectral waveform of the computed quantitative spectral intensity matrix X'kj and retention times of R'ik. Specifically, spectra of medicaments have previously been stored as a library such that the components are identified by searching the library. In continuation, at step 23, the component identification/quantification unit 457 performs quantification by the use of the magnitude of the matrix X'kj and with reference to the quantitative spectral intensity matrix of the standard sample 52.

At step 24, the results obtained from the steps described above are displayed on the CRT 46 and printed out by the printer 47 if so instructed by the operator. Specifically, the image before the deconvolution shown in FIG. 3B, the images of respective reconvoluted components (FIGS. 4A, 4D, 4F), and images of spectra of the respective components (FIGS. 5A, 5B, 5C) are displayed. In this event, the image before the deconvolution shown in FIG. 3B may be displayed such that the components 2, 3, which are the overlapping peaks, are represented in different colors from each other to clarify the overlapping. Then, the flow is terminated at step 25.

According to the first embodiment as described above, data constituting a multichannel chromatogram is compressed in the wavelength direction to remove noise components included therein. Then, the convolution is performed on the noise-free two-dimensional data. It is therefore possible to realize a method and apparatus for analyzing a multichannel chromatogram which accurately resolve overlapping peaks of a multichannel chromatogram for analyzing the overlapping peak components.

Also, according to the first embodiment, respective components separated by the deconvolution are reconvoluted with a device function. Then, the reconvoluted components are respectively displayed, and images representing the data not separated are displayed in different colors based on the respective reconvoluted components. The distinction of the components with different colors provides the operator with an image which clearly represents at which position components are overlapping.

Further, according to the first embodiment, the deconvolution is equivalent to obtaining matrices R'ik, S'ik by adding a certain type of deformation to a peak form, so that the analysis can be made free from a model function.

Figure 7:
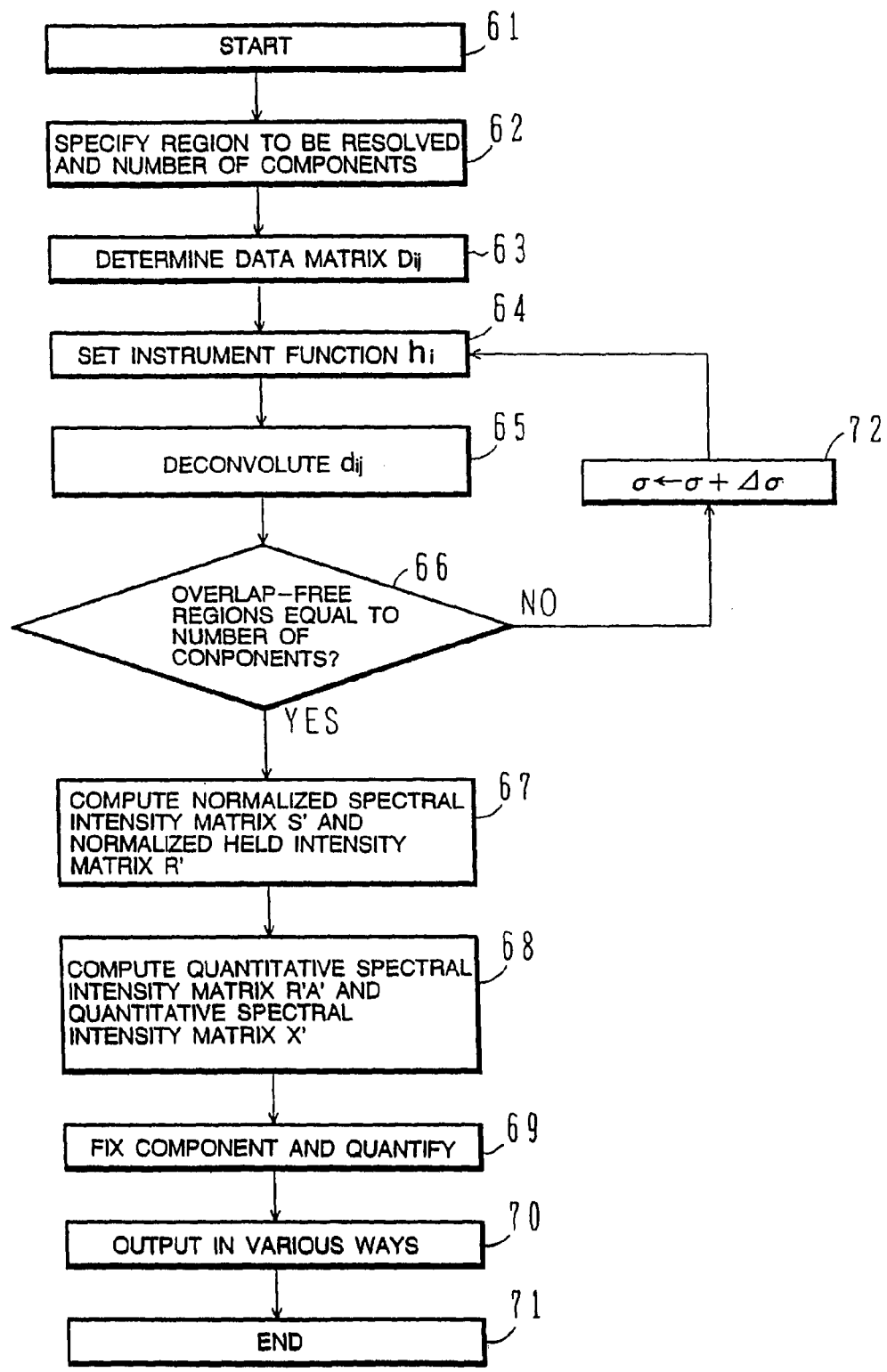
FIG. 7 is an operational flow chart representing a method for analyzing a multichannel chromatogram according to a second embodiment of the present invention.
Figure 8:
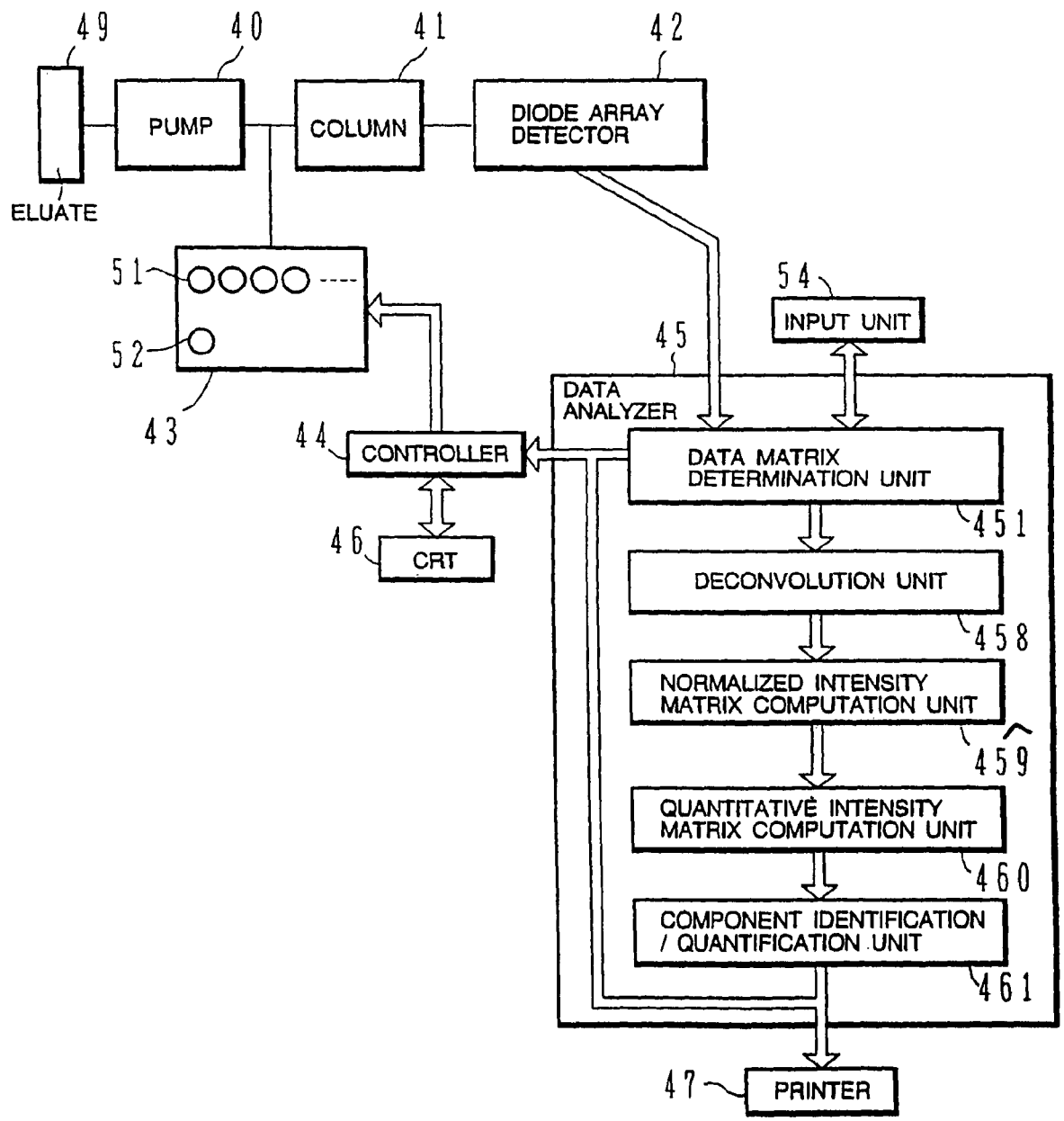
FIG. 8 is a block diagram schematically showing the configuration of an apparatus for analyzing a multichannel chromatogram according to the second embodiment of the present invention.

FIG. 7 is an operational flow chart representing the procedure of a method for analyzing a multichannel chromatogram according to a second embodiment of the present invention, and FIG. 8 is a block diagram schematically showing the configuration of an apparatus for analyzing a multichannel chromatogram according to the second embodiment of the present invention.

Referring to FIG. 8, a data analyzer 45 comprises a data matrix determination unit (data setting unit) 451, a deconvolution unit 458, and a normalized intensity matrix computation unit (data compression unit) 459. The data analyzer 45 further comprises a quantitative intensity matrix computation unit 460 and a component identification/quantification unit 461. The rest of the configuration is similar to corresponding portions shown in FIG. 2, so that explanation thereon will be omitted.

Referring next to FIG. 7, the flow starts at step 61. Next, at step 62, the data matrix determination unit 451 is supplied with regions in the time and wavelength directions in a multichannel chromatogram including overlapping peaks to be separated or resolved, for specifying data subjected to the subsequent processing. In this event, while the region is generally specified by inputting values corresponding to a start point and an end point of the region on the chromatogram, graphical manipulations on the screen of the CRT 46 may also be utilized. Specifically, the region may be specified by moving a cursor over lines on a contour plan representing the chromatogram on the CRT 46. Also, at this step 62, the number of components included in overlapping peaks in the specified region is inputted in the form of numerical values.

At step 63, the data matrix determination unit 451 determines the boundary of a data matrix Dij from the start and end points in the respective time and wavelength directions. In this embodiment, since deconvolution is performed prior to data compression, an appropriate number of points included between the start point and end point is approximately ten for both the time and wavelength directions.

Next, at step 64, the deconvolution unit 458 sets a device function hi($\sigma$). While a Gaussian device function is generally employed in a way similar to step 15 in FIG. 1, an actually measured dispersion function hi($\sigma$) may also be selected for the device function. It should noted however that if more intense deconvolution is to be performed in subsequent steps, a Gaussian device function will simplify the processing.

Then, at step 65, the deconvolution unit 458 performs convolution similar to that at step 16 shown in FIG. 1. In the present step, however, since the data matrix Dij is not compressed, approximately 100 points of data are subjected to the deconvolution.

Next, at step 66, the deconvolution unit 458 determines whether or not the number of overlap free regions is equal to the number of components, in other words, whether the deconvolution was sufficient. The criterion for the determination is such that if spectra are isolated as shown by areas k=2 and k=3 in FIG. 6, the deconvolution unit 458 determines that these are overlap free regions and the deconvolution was sufficient. As a condition, it is desirable that an area such as k=2 or k=3 includes three points or more.

As a special case, only one component of peaks appears in a certain wavelength area as shown in FIG. 5 as a summation area for deconvoluted data r'i3. From the deconvoluted data r'i3, one of convoluted data R'i3 can be obtained, and the other data R'i2 can be determined from the data R'i3. Of course, if respective peaks are isolated by the deconvolution, each convoluted data R'ik is obtained, so that the deconvolution is determined to be sufficient.

While the deconvolution may be iterated until overlapping peaks are isolated at steps 65 and 66, it is sufficient to perform the deconvolution in such a degree that a spectral intensity matrix S'kj, later described, can be accurately obtained. Note that if overlapping peaks can be resolved in such a degree that they are isolated at any wavelength, a normalized retention intensity matrix R'ik is obtained, so that the flow of this embodiment can also transfer to the method according to the first embodiment shown in FIG. 1. If it is determined at step 66 that the deconvolution was insufficient, the flow proceeds to step 72, where the width of the standard deviation $\sigma$ is slightly extended to update the device function hi($\sigma$). Then, the flow loops back to step 64. If it is determined at step 66 that the number of overlap free regions is equal to the number of components, the flow proceeds to step 67.

Figure 6:
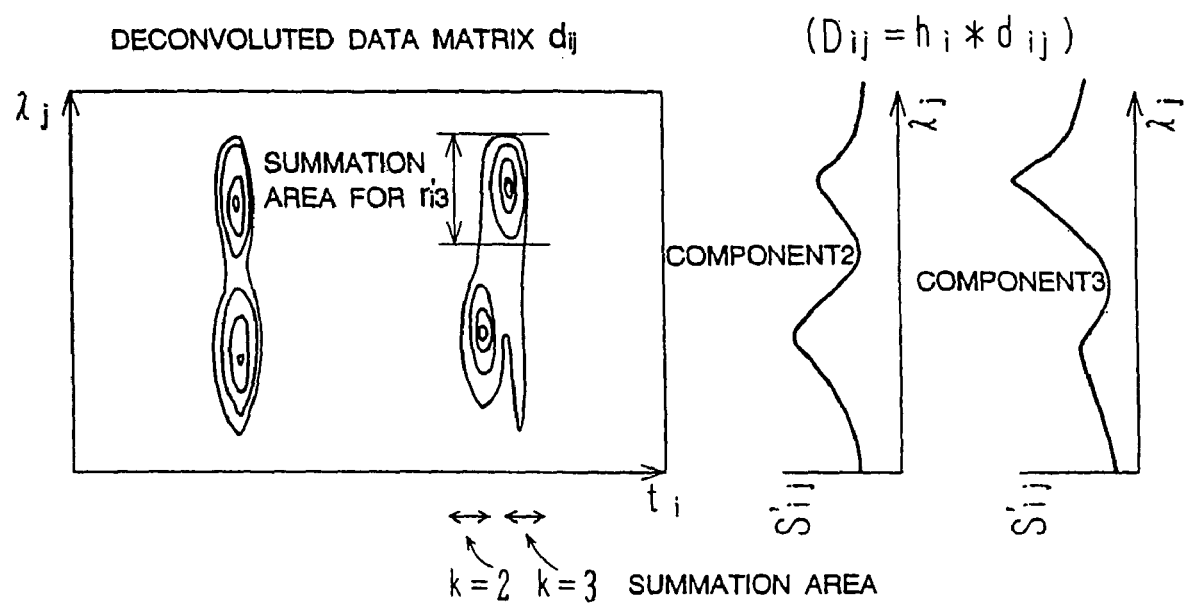
FIG. 6 shows waveforms of a deconvoluted data matrix.

At step 67, the normalized intensity matrix computation unit 459 computes a normalized spectral intensity matrix S'kj in accordance with the following equations (27-1) and (27-2) to obtain spectra S'2j and S'3j as shown in FIG. 6:

$$D_{ij} = h_i * d_{ij} \tag{27-1}$$

$$S^1_{kj} = \left(\sum_{i=i1}^{i2} d_{ij}\right) / \left(\sum_j \sum_{i=i1}^{i2} d_{ij}\right) \tag{27-2}$$

The data matrix Dij is computed based on the aforementioned equation (27-1), and the computed Dij is substituted in the equation (27-2) to compute a normalized spectral intensity matrix S'kj. In the equation, $i_1$ and $i_2$ designate a start point and an end point of a region in the chromatogram in which the spectrum of a k-component is obtained.

Then, if peaks are isolated in the time axis direction, a normalized retention intensity matrix R'ik is computed in accordance with the following equation (28).

$$R^1_{ik} = \left(\sum_{j=j1}^{j2} d_{ij}\right) / \left(\sum_i \sum_{j=j1}^{j2} d_{ij}\right) \tag{28}$$

where $j_1$ and $j_2$ designate a start point and an end point of a wavelength region in which a retention function for the k-component is obtained.

As described above, a multichannel chromatogram generally includes a lot of noise components. It can be thought that the noise components positively and negatively oscillate in the time axis direction. Therefore, if three-dimensional data of the multichannel chromatogram undergoes summation in the time axis direction, the noise components will cancel with each other, resulting in noise-free normalized spectral intensity matrix S'kj and normalized retention intensity matrix R'ik.

Next, at step 68, the quantitative intensity matrix computation unit 460 computes a quantitative retention intensity matrix R'ikA'kk based on the following equation (29):

$$R'A' = DS'^T(S'S'^T)^{-1} \tag{29}$$

Also, at step 67, if the normalized retention intensity matrix Rik has been computed, a quantitative spectral intensity matrix X'kj is computed based on the following equation (30):

$$X' = (R'^T R')^{-1} R'^T D \tag{30}$$

Then, the component identification/quantification unit 461 utilizes the computed spectral intensity matrix and the retention intensity matrix to identify components and quantify the identified components similarly to steps 22 and 23 in FIG. 1.

Next, at step 70, the results obtained by the foregoing steps are displayed on the CRT 45, similarly to step 24 in FIG. 1, and printed out if so instructed by the user. The processing is completed at step 71.

As described above, according to the second embodiment of the present invention, three-dimensional data of a multichannel chromatogram is compressed in the time axis direction to remove noise components therefrom, thus enabling the computation of noise-free normalized spectral intensity matrix S'kj and normalized retention intensity matrix R'ik. It is therefore possible to realize a method and apparatus for analyzing a multichannel chromatogram which can accurately resolve overlapping peaks in a multi-channel chromatogram for analyzing the components of a sample, similarly to the first embodiment shown in FIGS. 1 and 2.

The processing according to the second embodiment, like the embodiment shown in FIGS. 1 and 2, can be performed without relying on a model function.

It can be thought from a different point of view that the second embodiment of the present invention supports and extends a conventionally well-known method for obtaining spectra of components from lower portions or bases (less influenced by the overlapping) of overlapping peaks and resolving the peaks with the aid of the deconvolution. The embodiments of the present invention permit the resolution of overlapping peaks including three or more components, which has been difficult to be accomplish with the prior art techniques.

Figure 9A:
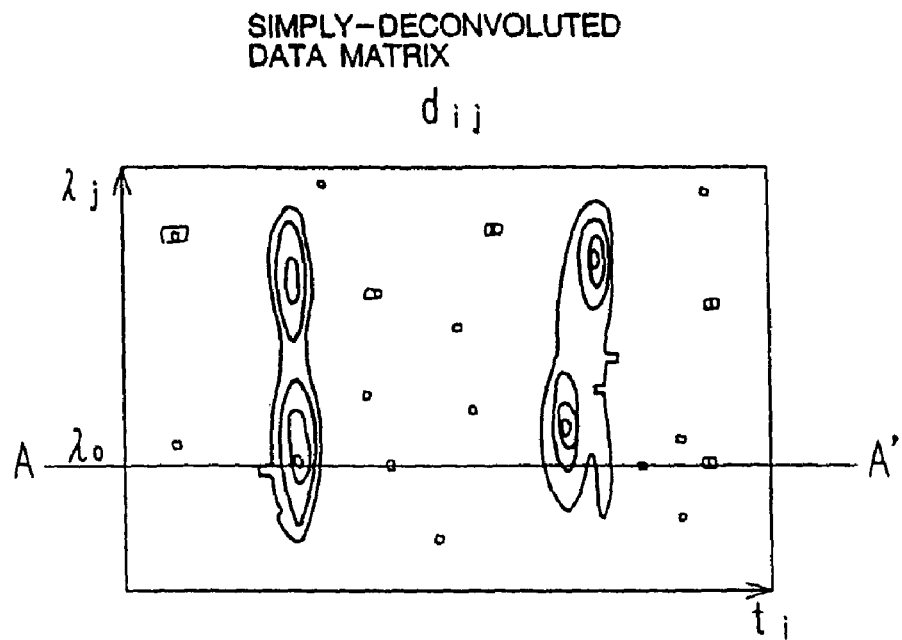
FIGS. 9A and 9B are waveform charts for comparing the present invention with the prior art.
Figure 9B:
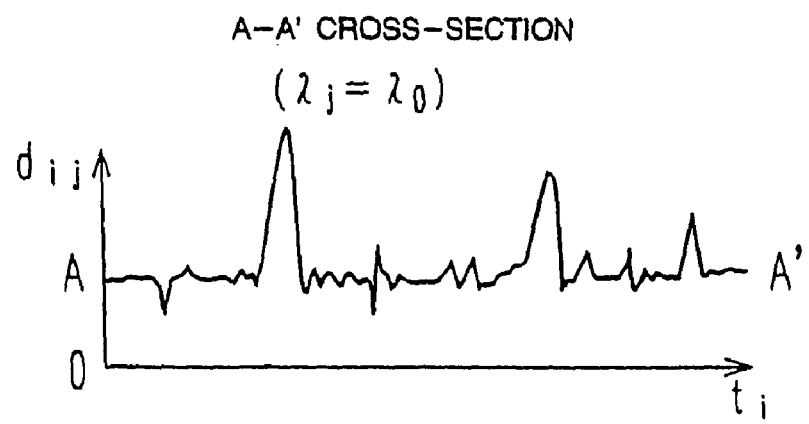

FIGS. 9A, 9B show an example of a graphical representation of a three-dimensional chromatogram obtained by deconvolution without data compression, for the purpose of comparing the present invention with the prior art techniques. As can be seen from FIGS. 9A, 9B, deconvolution simply performed on a three-dimensional chromatogram will cause noise and pseudo peaks to appear. FIG. 9B shows a cross-section taken along a line A-A' in FIG. 9A. It is understood that a simply deconvoluted three-dimensional chromatogram is equivalent to different two-dimensional chromatograms with several different wavelengths. Thus, simple convolution without data compression is far from making good use of whole information obtained from a three-dimensional chromatogram or appropriately processing the information, and cannot eliminate the disadvantage of anplified noise and pseudo peaks involved in the conventional two-dimensional chromatogram.

In contrast, the present invention additionally executes data compression such that noise components cancel with each other to eliminate the noise components from a three-dimensional chromatogram, thus overcoming the disadvantage inherent to the prior art techniques.

It should be noted that in the foregoing embodiments, normal smoothing and baseline processing are performed during the deconvolution as required.

The data analyzer 45 may be supplied from the input unit 54 with a plurality of estimated retention times and an initial value of a fitting parameter for a time constant for specifying a tailing peak, in addition to an initial value for a standard deviation of a device function.

Since the first and second embodiments of the present invention are configured as described above, the following effects are expected.

A multichannel chromatogram is compressed in terms of the wavelength component to be transformed into two-dimensional chromatogram data from which noise components are removed. The two-dimensional chromatogram data having noise components removed therefrom is deconvoluted to remove data dispersion caused by the device function, whereby overlapping peaks are accurately resolved. Then, components of a sample under measurement are identified based on the accurately resolved data. It is therefore possible to realize a method and apparatus for analyzing a multichannel chromatogram which can accurately resolve overlapping peaks in a multichannel chromatogram for analyzing the components of the sample under measurement.

Alternatively, multichannel chromatogram data is first deconvoluted. Then, the deconvoluted multichannel chromatogram data is compressed in terms of the time component for the respective components to compute spectral information on the respective components. In this compression, noise components cancel with each other so that they are removed from the data. Then, components of a sample are identified based on the spectra from which noise components have been removed. It is therefore possible, similarly to the foregoing, to realize a method and apparatus for analyzing a multichannel chromatogram which can accurately resolve overlapping peaks in a multichannel chromatogram for analyzing the components of the sample under measurement.

Figure 10:
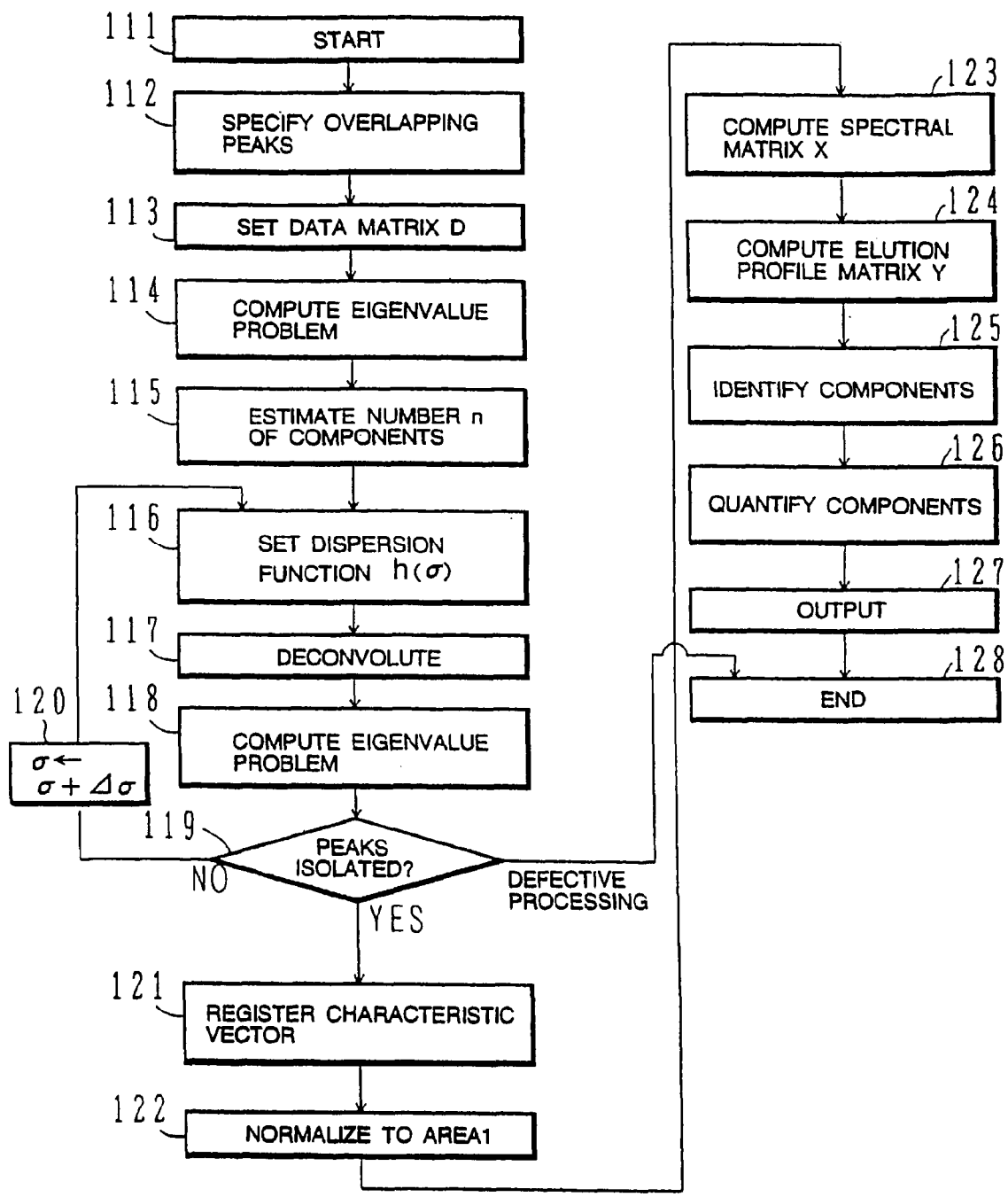
FIG. 10 is an operational flow chart representing a method for analyzing a multichannel chromatogram according to a third embodiment of the present invention.
Figure 11:
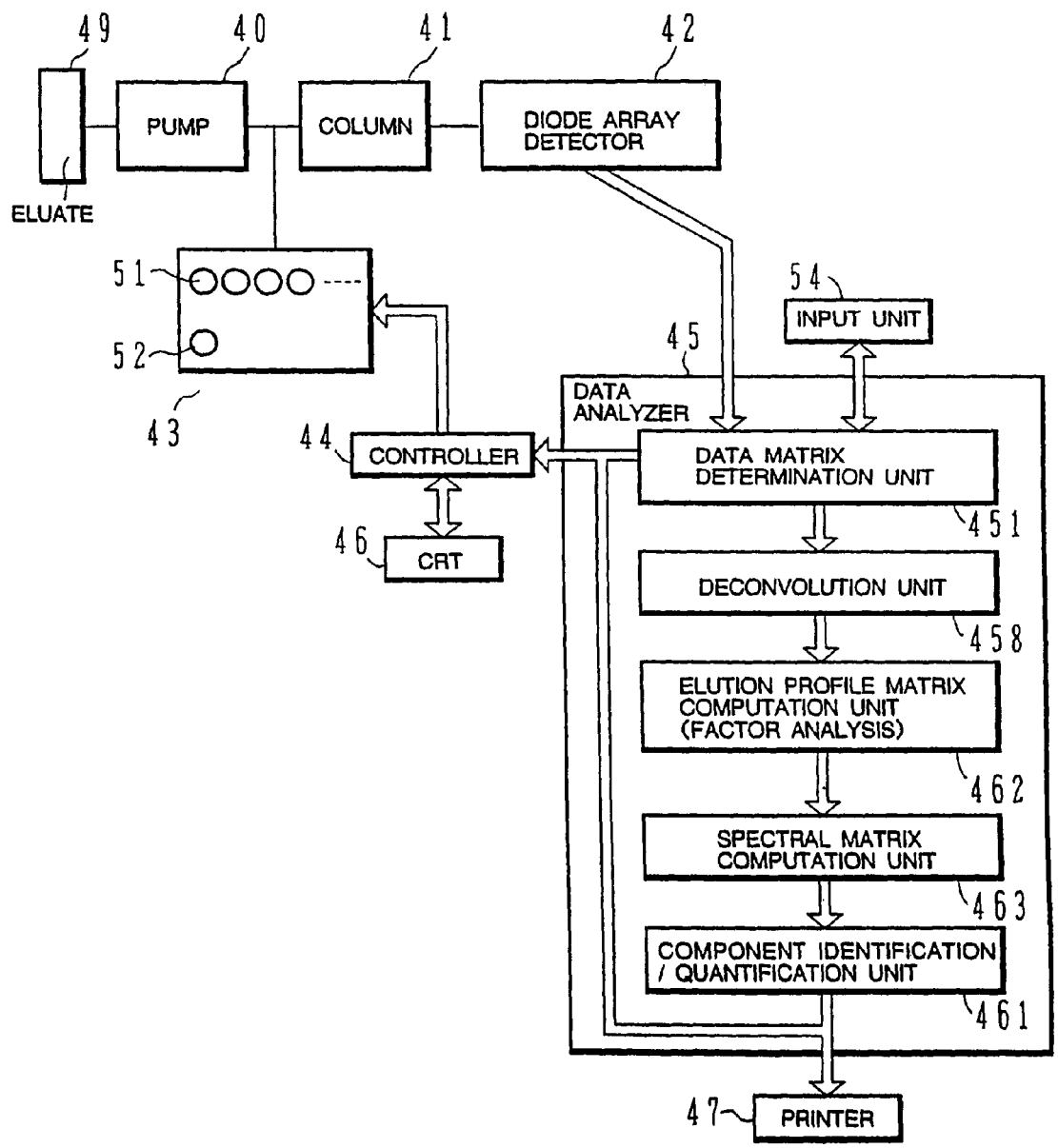
FIG. 11 is a block diagram schematically showing the configuration of an apparatus for analyzing a multichannel chromatogram according to the third embodiment of the present invention.

FIG. 10 is an operational flow chart representing the procedure of a method for analyzing a multichannel chromatogram according to a third embodiment of the present invention, and FIG. 11 is a block diagram schematically showing the configuration of an apparatus for analyzing a multichannel chromatogram according to the third embodiment of the present invention. The configuration of FIG. 11 is an example wherein the present invention is applied to a medicament monitoring HPLC system, similarly to the first embodiment shown in FIG. 2.

Referring in detail to FIG. 11, a pump 40 delivers an eluate 49 in response to a command from a controller 44. A sampler 43 having a movable needle injects a standard sample 52 stored in a sample container or an unknown sample (sample under measurement) 51 into a channel of a column 41. The sample 51 or 52 is introduced into the column 41 together with the eluate 49, so that components of the sample is separated and detected by a diode array detector 42. The detected data, i.e., multichannel chromatogram is supplied to a data analyzer 45.

The data analyzer 45 is also supplied with components and so on, later described, from an input unit 54. Then, the results of analysis made in the data analyzer 45 are displayed on CRT 46 and printed out by a printer 47.

The data analyzer 45 comprises a data matrix determination unit (data setting unit) 451, a deconvolution unit 458, an elution profile matrix computation unit (factor analysis unit) 462, a spectral matrix computation unit 463, and a component identification/quantification unit 461.

Figure 12:
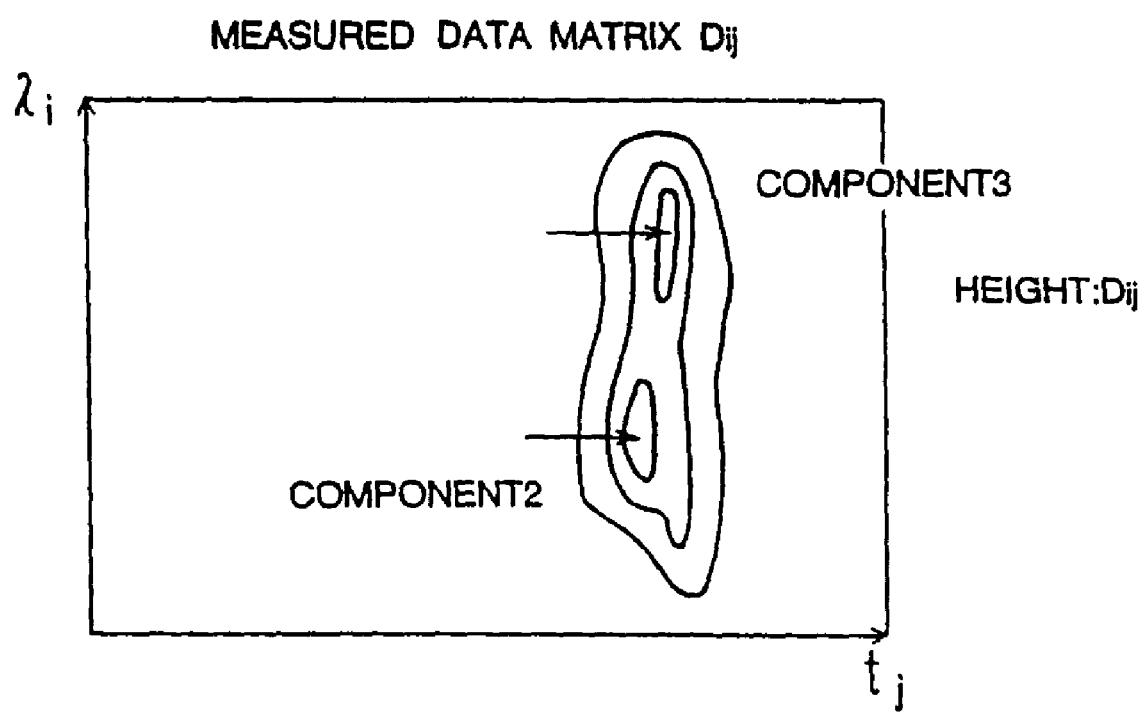
FIG. 12 is a diagram showing an example of a displayed multichannel chromatogram data.

FIG. 12 shows a multichannel chromatogram of the unknown sample 51 obtained by the present system. When an organic sample is to be measured as does the present system, unknown miscellaneous peaks may appear and often overlap with each other. Specifically, in FIG. 12, overlapping components 2, 3 make it difficult to perform not only quantification but also component identification. It is therefore necessary to separate or resolve the overlapping peaks to correctly obtain retention times and accurately obtain spectra in order to identify the components. In addition, by correctly determining magnitudes of respective peaks, quantitative analysis can be also carried out from a comparison with the standard sample 52.

The operation performed after a multichannel chromatogram has been obtained from the diode array detector 42, computation algorithms employed in the operation, and output of the results will be orderly explained with reference to a flow chart of FIG. 10.

The flow starts at step 111 in FIG. 10. At step 112, overlapping peaks to be separated or resolved are specified. A contour plan representing a three-dimensional chromatogram as shown in FIG. 12 is displayed on the CRT 46. Components 2 and 3 are inputted by indicating these regions with an arrow generated by the input unit 54 which may be a mouse, a pen, or the like. Alternatively, coordinates of the components 2, 3 may be directly inputted in the form of numerical values or by moving a cursor over lines on the display.

At step 113, a search is made for a start point and an end point of the whole region including the specified overlapping peaks to determine time points of a data matrix D corresponding to the searched start and end points. An appropriate number of points to be measured from the start point to the end point is in the range of 20-30. If the number of points is greater than this range, the number of points is desirably reduced by addition average or the like. As to the number of points in the wavelength direction, the number of measured channels is simply employed. Alternatively, the number of points in the wavelength direction may be reduced by addition average or thinning.

Figure 13A:
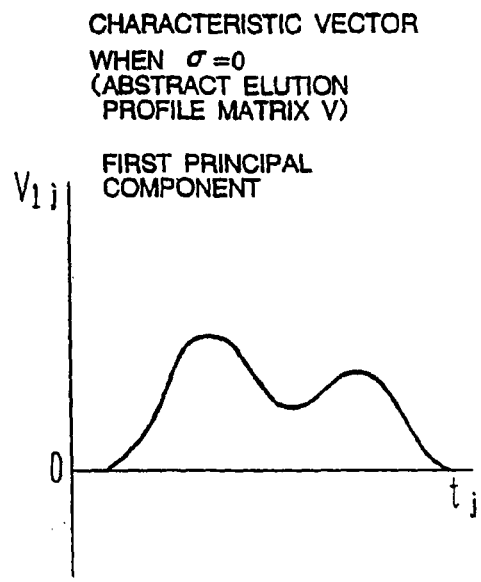
FIGS. 13A-13H are waveform charts showing changes in a characteristic vector and an elution profile matrix before and after deconvolution.
Figure 13B:
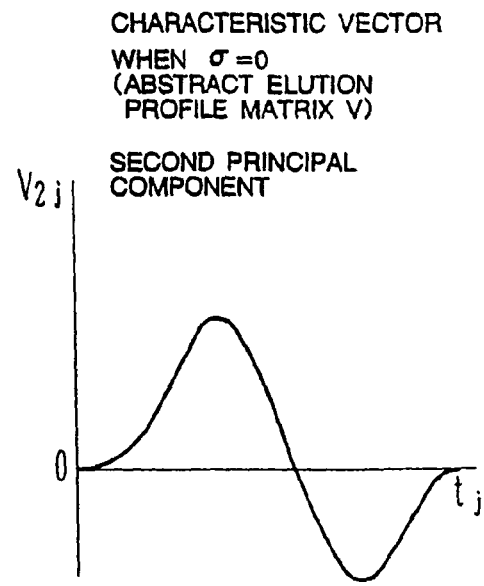
Figure 13C:
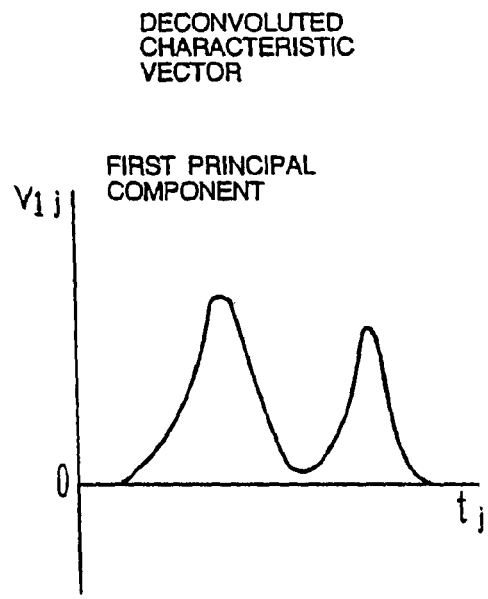
Figure 13D:
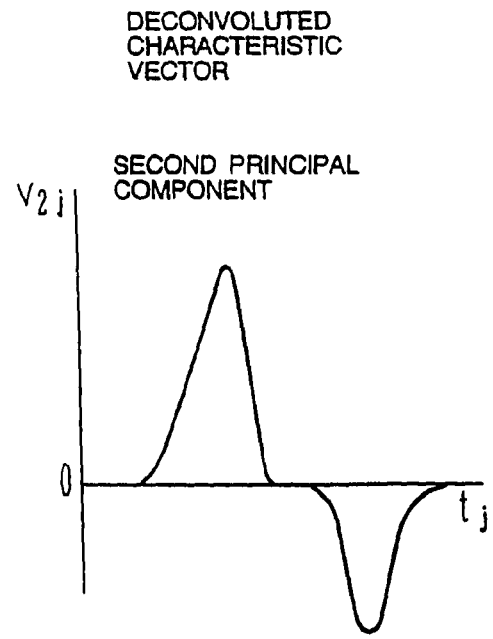
Figure 13E:
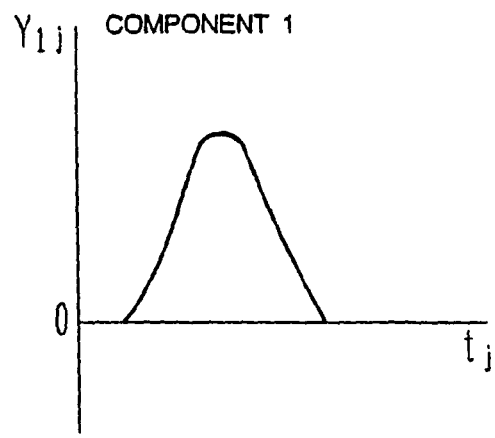
Figure 13F:
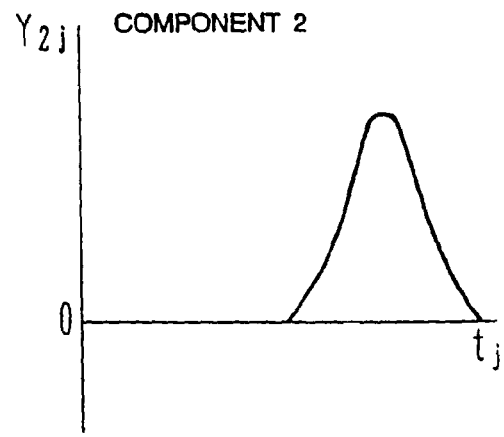
Figure 13G:
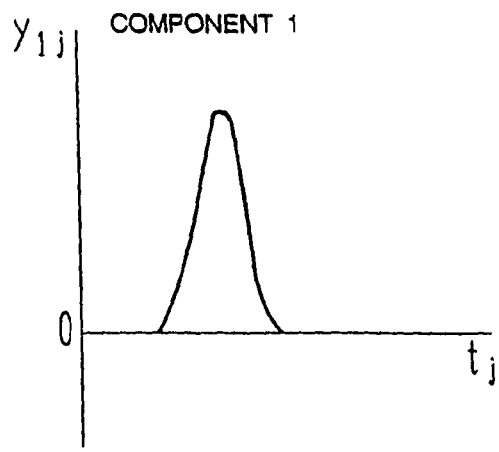
Figure 13H:
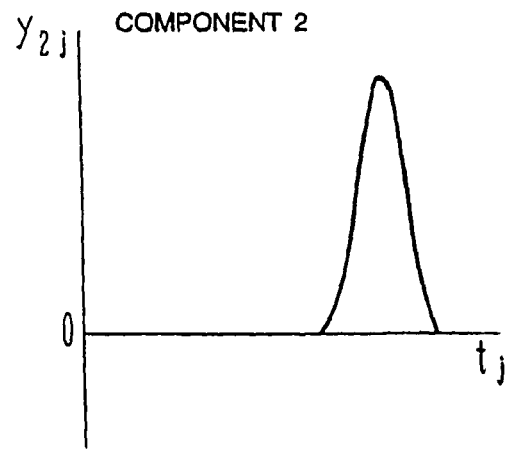

At step 114, an eigenvalue problem is solved, and characteristic values and characteristic vectors are computed. As shown in the equation (7), a matrix Z is obtained from the matrix D, and characteristic values $\zeta$ and characteristic vectors v are computed (FIG. 13A). The maximum characteristic value is designated $\zeta$max. For convenience, components, for example, having the characteristic value equal to or more than ($\zeta$max/100) are counted in order to determine the number n of components at step 115. In this embodiment, n is equal to two (n=2).

Next, a matrix T is estimated for transforming a matrix V having the characteristic vector v in its row component to an elution profile matrix Y. Here, "varimax" is utilized as an estimation method. Since "varimax" is based on the operation for approximating a load amount to ±1 or zero for each row vector after transformation (See "Multivariate Analysis-Based Method (Revised Edition)" by Chuichi Okuno et al, published by Nikka Giren Shuppan-sha, pp. 323-372, (1992)), the obtained matrix Y can be assumed to substantially reflect individual pulsatile elution profiles. Actually, the matrix T is also provided with a function of normalizing the matrix Y to area 1.

Figure 15:
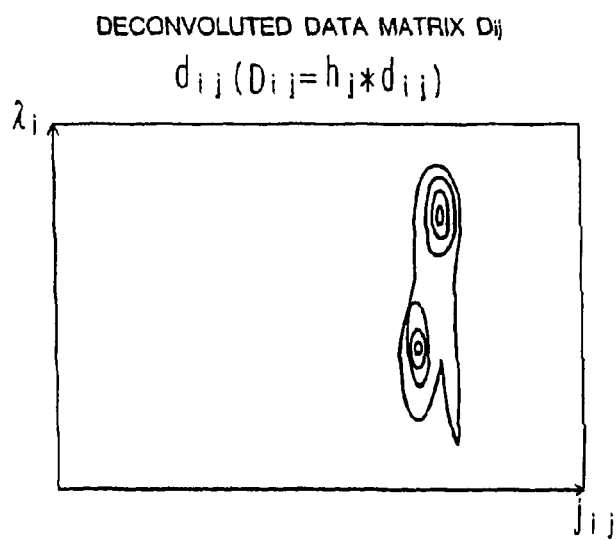
FIG. 15 is a waveform chart showing a deconvoluted data matrix.

Next, the flow proceeds to a deconvolution stage. At step 116, a device function h($\sigma$) is set for use in the deconvolution. Employed as an initial value of standard deviation, $\sigma$ may be a fixed value or an input value, for example, 1,100 of the time width of the matrix D. As an alternative method, the determination at step 119 may be made with the initial value set to zero for trial. At step 117, the matrix D is deconvoluted with h($\sigma$) as expressed by the equation (16). For the deconvolution, any method such as Jansson's method may be utilized. Thus, a deconvoluted matrix d($\sigma$) is obtained (see FIG. 15).

Figure 16:
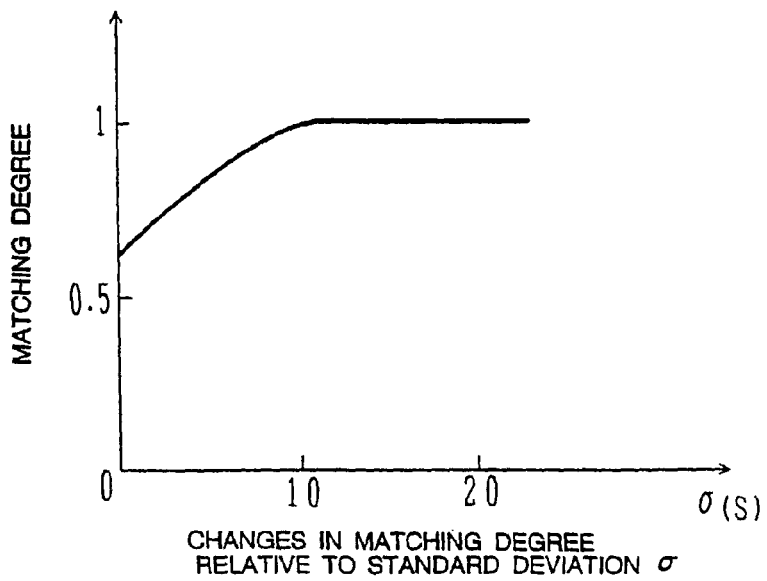
FIG. 16 is a graph showing changes in matching degree relative to standard deviation.

At step 118, characteristic values and characteristic vectors are computed for the matrix d as is the case of the matrix D, and then, the matrix d is transformed to a matrix y using the matrix T in accordance with the criterion of "varimax". A spectral matrix X corresponding to the matrix y is computed in accordance with the aforementioned equations d=Xy, $X=dy^T(yy^T)^{-1}$. It is determined at step 119 whether peaks in the matrix d are sufficiently separated from each other, i.e., isolated. The step 119 determines that peaks are sufficiently separated when the matrix X obtained at step 118 is coincident with a previously obtained matrix X. In the first execution of the flow, the matrix X obtained based on the matrix D is compared. In the second and subsequent executions, the deconvoluted matrix d obtained in the present loop is compared with the deconvoluted matrix d obtained in the previous loop. The matching degree is generally determined by a correlation coefficient (see FIG. 16).

Essentially, comparison of the matching degree between the present and previous matrices X is equivalent to comparison of a rotating angle of transformation. While the matrix T has functions of rotation R and normalization N in this embodiment, comparison of the rotating transformation matrix R only becomes equivalent.

Figure 17:
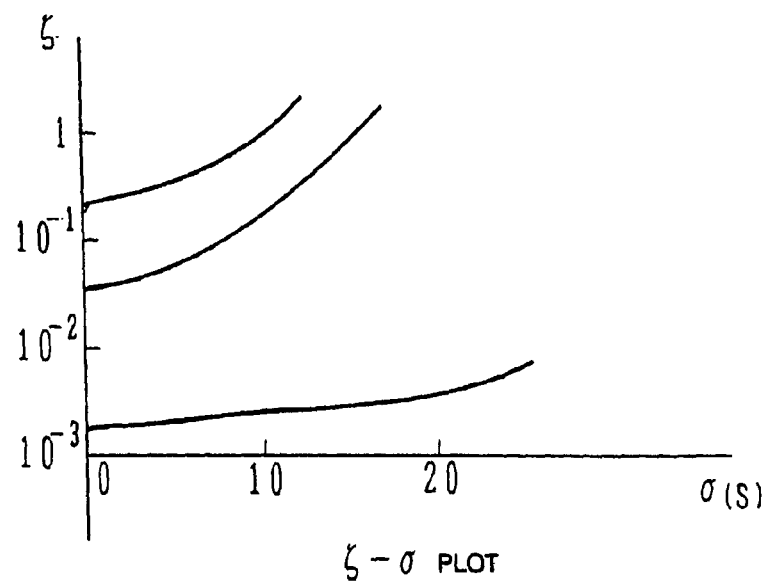
FIG. 17 is a graph representing the relationship between $\zeta$ and the standard deviation $\sigma$.
Figure 18:
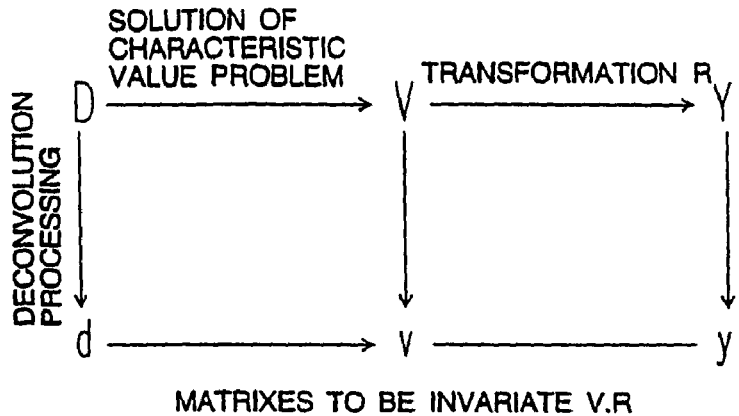
FIG. 18 is a schematic diagram for evaluating the appropriateness of the deconvolution.
Figure 19:
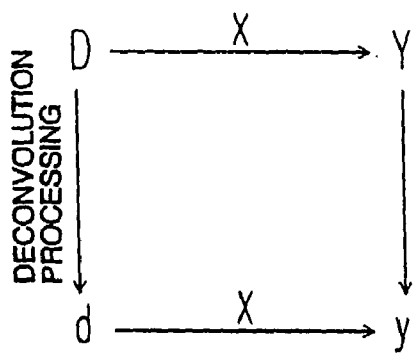
FIG. 19 is a schematic diagram for evaluating the appropriateness of the entire DFA.

In addition, the above-mentioned number of components can be automatically determined by utilizing a $\zeta$-$\sigma$ plot representing the relationship between the characteristic values $\zeta$ and the standard deviation $\pi$ (see FIG. 17). As $\sigma$ is gradually extended, changes in $\zeta$ are measured. It can be seen from FIG. 17 that two large characteristic values monotonously increase as $\sigma$ is larger. This trend is caused by the peak waveforms which are made sharper by the deconvolution. Taking advantage of this nature, the number of components can be determined by counting characteristic values which monotonously increase with increasing $\sigma$.

Turning back to step 119, if isolated peaks are recognized, the flow proceeds to step 121. Otherwise, the flow proceeds to step 120 where the standard deviation $\sigma$ is increased, and deconvolution is again attempted. For an increment $\Delta\sigma$, the above-mentioned initial value of the standard deviation is used by way of example. In case abnormally gigantic pseudo peaks appear, the occurrence of defective processing is determined, so that an error signal is generated followed, by the termination of the flow.

At step 121, a finally determined matrix d($\sigma$) is registered when the determination at step 119 indicates YES. At step 122, each characteristic vector is orthogonally rotated and normalized such that its area (the sum) is equal to one. The normalized vector is assigned to a row vector of the deconvoluted elution profile matrix y.

Figure 14A:
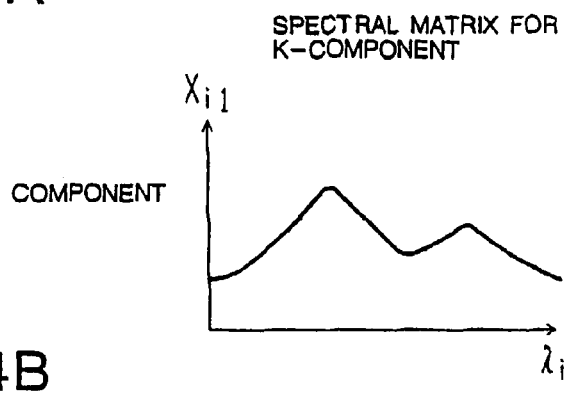
FIGS. 14A and 14B are waveform charts each showing a spectral intensity matrix for a component k.
Figure 14B:
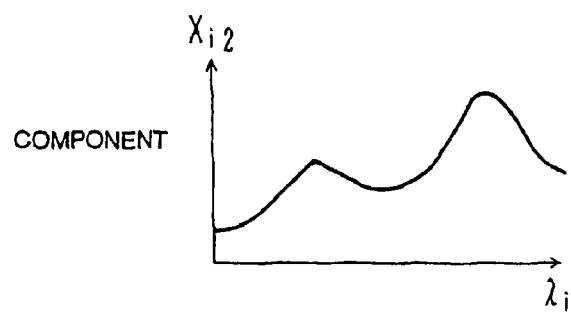

At step 123, a spectral matrix X is obtained in accordance with the equations (19) and (20) (see FIG. 14). At step 124, an elution profile matrix Y is computed in accordance with the equation (21). Components of the sample are identified based on the spectral waveforms of the matrix X and retention times of the matrix Y. For the component identification, spectra of medicaments have been previously stored as a library such that this library is searched for the components. At step 125, the components are quantified using the magnitude of the matrix X with reference to the spectral matrix of the standard sample 52.

At step 126, the results as shown in FIGS. 12-14 are displayed on the CRT 46 and may also be printed out if so instructed by the operator.

The flow is completed at step 127.

An oblique rotation based method has an advantage that smaller-scale deconvolution can be used to orderly perform rank annihilation. For example, instead of the aforementioned "varimax", "covarim" may be used as the criterion for performing the oblique rotation. If a spectral matrix can be estimated using a smaller standard deviation $\sigma$ prior to the deconvolution with a standard deviation $\sigma$ which provides perfect isolation of overlapping peaks, faster rank annihilation is accomplished without amplifying noise.

The DFA analysis can be made immediately after data collection by previously set parameters. Here, explanation will be given of an operation procedure as secondary processing of data analysis. First, a three-dimensional chromatogram is read on the CRT (see FIG. 12). For resolving overlapping peaks, a time region, a wavelength region, and the numbers of points in row and column are inputted to define a data matrix D. Then, the eigenvalue problem is solved, and obtained characteristic values are displayed in order from the largest one.

The user estimates to which point from the largest one the characteristic values include meaningful components, and inputs the estimated number n of components. If rules have been previously established for the estimation, the number n of components may be automatically estimated. Alternatively, if the execution of rank annihilation is set, the processing can be advanced on the assumption that the number of components is two, unless otherwise specified. Next, the type of rotation transformation is selected. Generally, "varimax" is selected, whereas "covarimin" is selected if up to oblique rotation is allowed. Next, an increment $\Delta\sigma$ for the standard deviation $\sigma$ of the dispersion function is set to, for example, one second.

The DFA method according to the third embodiment of the present invention is advantageous over the compression method according to the first embodiment in the following aspects.

Figure 20:
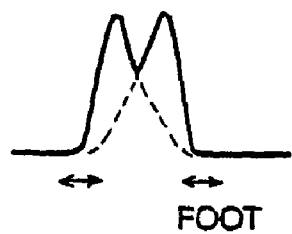
FIG. 20 is a waveform chart for explaining overlapping peaks including two components.

First, in the compression method, the isolation of peaks is critical. At least the base of a peak must purely consist of one component. Thus, it is necessary in the compression method to iterate the deconvolution until peaks are isolated or until chromatogram regions each purely consisting of one component appear. It can be said that the approach of iterating the deconvolution until spectra each consisting of one component are obtained is based on purity, from a viewpoint that the peaks are more sharpened until one-component spectra are obtained (see FIGS. 20 and 21).

On the other hand, the DFA method can be based on uniqueness. Stated another way, the deconvolution is stopped even if peaks have not been isolated, or even if purely one-component chromatogram regions do not exist, provided that factor analysis can uniquely have a resolution.

Figure 23:
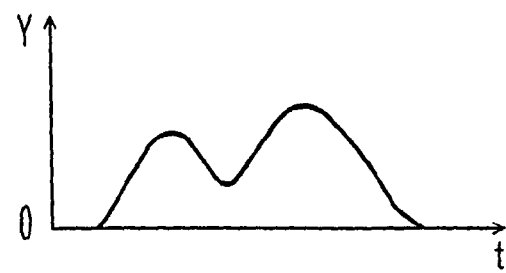
FIG. 23 is a graph showing an exemplary elution profile having two maximal values.

FIG. 23, for example, shows that a rotating angle of a rotation matrix R is indefinite in a region with a small standard deviation $\sigma$. In this example, a sole requirement is that the spectral matrix X and the elution profile matrix Y are both positive. For example, in a region where $\sigma$ is 6s or more, an indefinite region of a component 1 disappears, so that its rotating angle can be uniquely determined. The deconvolution is stopped based on this uniqueness, thus achieving the rank annihilation.

As described above, the DFA method requires less iterations of the deconvolution than the compression method. In addition, overlapping peaks can be resolved without adding much deformation to the original data matrix. This means that noise and distortion can be suppressed in the finally obtained spectra X and elution profiles Y (see FIG. 9).

Referring again to FIG. 22, the graph shows that factor analysis is still indefinite with small-scale deconvolution with the standard deviation $\sigma$ being 6s or less. It can be seen from FIG. 22 that the component 1 has a positive (non-negative) spectrum and a positive elution profile at any transformation angle around the rotating angle $\theta$ of 180°. Conversely, with a equal to 6s, the positive spectrum X and the positive elution profile Y can be obtained only at approximately 160°.

It can be understood that the rotating angle $\theta$ for the component 1 is indefinite with a less than 6s, whereas the angle $\theta$ can be uniquely obtained from a equal to 6s.

The deconvolution is stopped at this time the spectrum and elution profile are established for the component 1. Once the spectrum and elution profile for the component 1 have been established, the spectrum and elution profile for a component 2 can also be determined by the rank annihilation.

Figure 22:
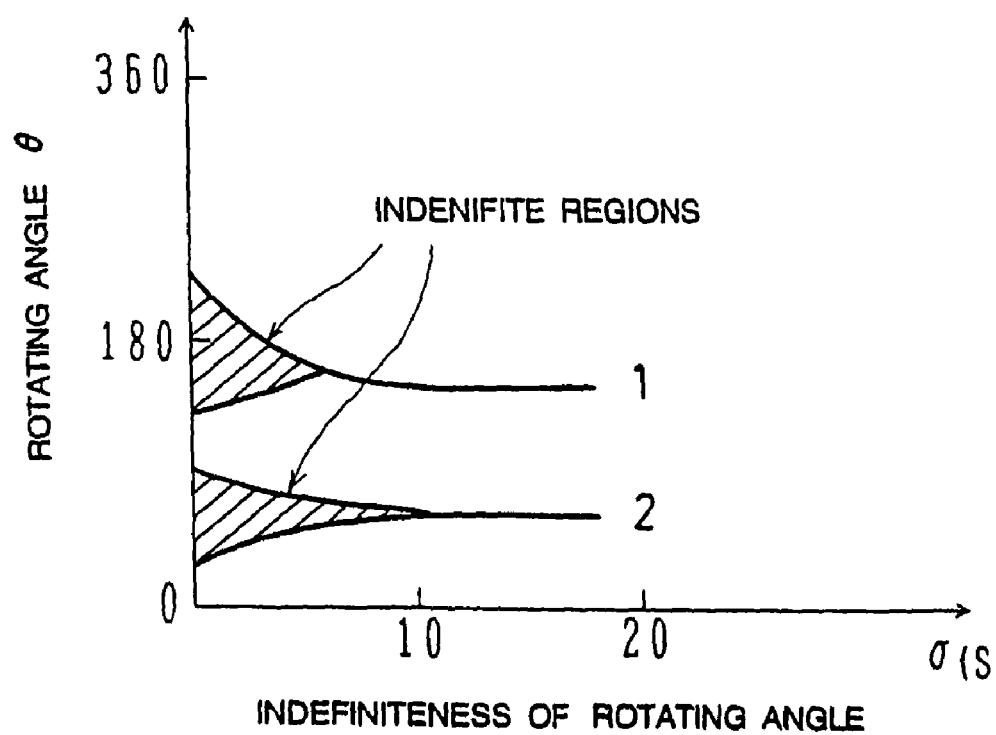
FIG. 22 is a graph for explaining indefiniteness of the rotating angle.

Explaining the results shown in FIG. 22 in detail, in a region where $\sigma$ is less than approximately 10s, solutions can be obtained by oblique rotation, and the component 2 does not yet present the uniqueness. With $\sigma$ being 10s or more, solutions can be obtained by orthogonal rotation. The difference in the angle $\theta$ between the components 1 and 2 is just 90°.

Here, the spectrum X and elution profile Y are conditioned that both are positive. However, although they are conditioned to be positive, fluctuations to a negative domain due to noise must be tolerated. Thus, it is assumed, in this embodiment, that negative values thereof up to approximately 1% of their maximum values are tolerated.

Under conditions that both the spectrum X and the elution profile Y are only positive, when two components have the same spectrum, an elution profile having two maximal values are presented as shown in FIG. 23. To prevent this, a condition of "unimodality" (only one peak per profile) is imposed to the shape of peak (see Anal. chem., No. 65, pp. 2040-2043, (1993)).

According to the third embodiment of the present invention as described above, a large amount of information provided by a multichannel chromatogram can be utilized to obtain spectra and elution profiles of unknown components. Then, from the obtained spectra and elution profiles, overlapping peaks can be separated or resolved, and component identification and quantification can be accurately accomplished for the components.

While the third embodiment has been described, by way of example, for a combination of deconvolution and factor analysis, the deconvolution may be combined with any of other multivariate analysis based methods, not limited to the factor analysis.

Specifically, regression analysis, which is one of such multivariate analysis based methods, may be combined with the deconvolution to improve a method for resolving overlapping peaks in a multichannel chromatogram. The aforementioned conventional non-linear least-squares method has more difficulties in determining a regression coefficient as more peaks are overlapping.

Therefore, if the regression analysis is applied to a deconvoluted data matrix d, a regression coefficient can be relatively easily determined since the deconvoluted data matrix d has less severely overlapping peaks than the original data matrix D. For restoring the respective original peak waveforms, the determined regression coefficient such as Gaussian is reconvoluted. Alternatively, another effective approach may be such one that estimates an initial value of the regression coefficient for the matrix D based on a regression function obtained by the reconvolution and again executes the regression analysis.

In the third embodiment of the present invention as described above, factor analysis may be executed after the data compression according to the first embodiment has been performed.

Figure 24:
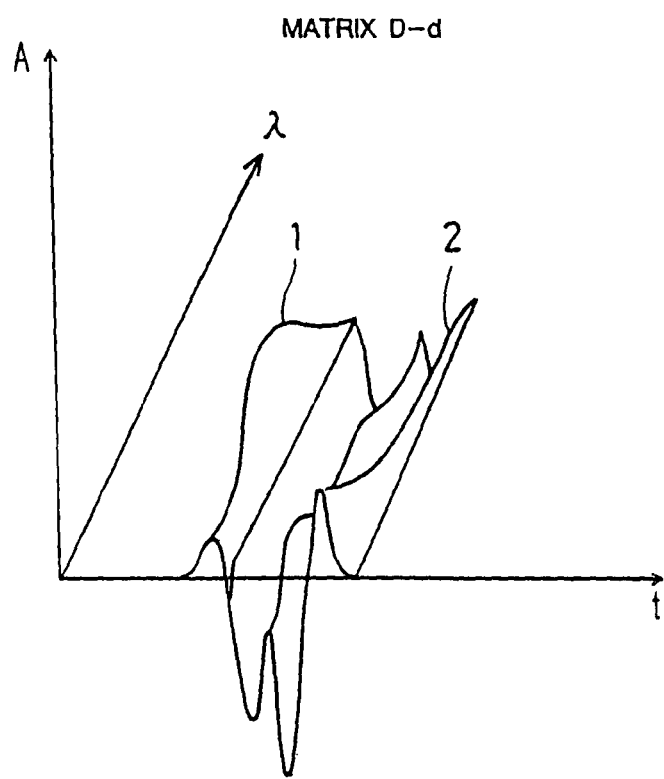
FIG. 24 is a graph for explaining an example which factor-analyzes a deconvoluted matrix.

Specifically, a spectrum obtained from a base portion of a peak may be used as a reference for determining a transformation matrix T in the factor analysis. Thus, a portion 1 or 2 in the difference D-d between an original matrix and a deconvoluted matrix (see FIG. 24) is compressed along the time axis t by summation to obtain a spectral waveform. A transformation matrix can be determined with the thus obtained spectral waveform serving as a known target.

Figure 21:
FIG. 21 is a waveform chart for explaining overlapping peaks including three components.

In this way, if a matrix is factor-analyzed after being compressed, the aforementioned factor analysis based method may be applied to the case where a sufficient spectrum cannot be obtained from a base of a peak. Specifically, factor analysis after compression may be effectively applied to the case where a spectrum of the middle peak is to be obtained when three or more peaks are overlapping, as shown in FIG. 21.

While the foregoing embodiment has been described as an example of applying the present invention to a medicament monitoring HPLC system, the present invention is not limited to this system but can be applied to other chroinatographic analysis system.

In addition, while a characteristic component of a sample under measurement is selected to be absorbance in the foregoing embodiments, the present invention is applicable when fluorescent magnitude is specified as a characteristic component.

Further, multichannel chromatogram includes three-dimentional intensity components of quantitative intensity, retention intensity and qualitative intensity such as wave length component, fluorescent wave length, mass unit (m/z) of a mass spectrograph, oxidation-reduction potential of an electrochemistry detector (ECD) or the like. Those quantitative intensities can be applied to this invention.

What is claimed is:

1. A data processing apparatus for analyzing overlapping peaks on a multi-channel chromatogram, comprising:
    a computation unit for adjusting a dispersion function by a deconvolution operation with changing a deconvoluting parameter from said dispersion function until a multivariate analysis uniquely has a solution, determining a multi-channel chromatogram deconvoluted by using a dispersion function adjusted by said deconvolution operation, and analyzing overlapping peaks on said multi-channel chromatogram deconvoluted by said dispersion function.

2. A data processing apparatus according to claim 1, wherein said computation unit measures peak sizes in the determined multi-channel chromatogram, performing a quantitative analysis.

3. A data processing apparatus according to claim 1, wherein said computation unit measures retention times on the basis of the determined multi-channel chromatogram, performing a qualitative analysis.

4. A data processing apparatus according to claim 1, wherein said computation unit reconvolutes the deconvoluted multi-channel chromatogram, measuring peak sizes of the reconvoluted multi-channel chromatogram, performing a quantitative analysis.

5. A data processing apparatus according to claim 1, wherein said computation unit reconvolutes the deconvoluted multi-channel chromatogram, measuring retention times of the reconvoluted multi-channel chromatogram, performing a qualitative analysis.

6. A data processing apparatus according to claim 1, wherein said computation unit compresses the deconvoluted multi-channel chromatogram, measuring peak sizes of the compressed multi-channel chromatogram, performing a quantitative analysis.

7. A data processing apparatus according to claim 1, wherein said computation unit compresses the deconvoluted multi-channel chromatogram, measuring retention times of the compressed multi-channel chromatogram, performing a qualitative analysis.

8. A data processing apparatus according to claim 1, wherein said computation unit reconvolutes the deconvoluted multi-channel chromatogram, compressing the reconvoluted multi-channel chromatogram, measuring peak sizes of the compressed multi-channel chromatogram, performing a quantitative analysis.

9. A data processing apparatus according to claim 1, wherein said computation unit reconvolutes the deconvoluted multi-channel chromatogram, compressing the reconvoluted multi-channel chromatogram, measuring retention times of the compressed multi-channel chromatogram, performing a qualitative analysis.

10. A method for analyzing overlapping peaks on a multi-channel chromatogram, comprising:
    adjusting, using a data processing apparatus, a dispersion function by a deconvolution operation with changing a deconvoluting parameter from said dispersion function until a multivariate analysis uniquely has a solution;
    determining, using the data processing apparatus, a multi-channel chromatogram deconvoluted by using a dispersion function adjusted by said deconvolution operation; and
    analyzing, using the data processing apparatus, overlapping peaks on said multi-channel chromatogram deconvoluted by said dispersion function.

11. The method of claim 10, further comprising:
measuring peak sizes in the determined multi-channel chromatogram, performing a quantitative analysis.

12. The method of claim 10, further comprising:
measuring retention times on the basis of the determined multi-channel chromatogram, performing a qualitative analysis.

13. The method of claim 10, further comprising:
reconvoluting the deconvoluted multi-channel chromatogram; measuring peak sizes of the reconvoluted multi-channel chromatogram, performing a quantitative analysis.

14. The method of claim 10, further comprising:
reconvoluting the deconvoluted multi-channel chromatogram, measuring retention times of the reconvoluted multi-channel chromatogram, performing a qualitative analysis.

15. The method of claim 10, further comprising:
compressing the deconvoluted multi-channel chromatogram, measuring peak sizes of the compressed multi-channel chromatogram, performing a quantitative analysis.

16. The method of claim 10, further comprising:
compressing the deconvoluted multi-channel chromatogram, measuring retention times of the compressed multi-channel chromatogram, performing a qualitative analysis.

17. The method of claim 10, further comprising:
reconvoluting the deconvoluted multi-channel chromatogram, compressing the reconvoluted multi-channel chromatogram, measuring peak sizes of the compressed multi-channel chromatogram, performing a quantitative analysis.

18. The method of claim 10, further comprising:
reconvoluting the deconvoluted multi-channel chromatogram, compressing the reconvoluted multi-channel chromatogram, measuring retention times of the compressed multi-channel chromatogram, performing a qualitative analysis.

19. A multi-channel chromatographic analyzer comprising:
    a data processing apparatus for analyzing overlapping peaks on a multi-channel chromatogram, and
    a computation unit for adjusting a dispersion function by a deconvolution operation with changing a deconvoluting parameter from said dispersion function until a multivariate analysis uniquely has a solution and determining a multi-channel chromatogram deconvoluted by using a dispersion function adjusted by said deconvolution operation.

20. The multi-channel chromatographic analyzer of claim 19, wherein said computation unit measures peak sizes in the determined multi-channel chromatogram, performing a quantitative analysis.

* * * * *